(12) United States Patent
Itu et al.

(10) Patent No.: US 10,297,341 B2
(45) Date of Patent: May 21, 2019

(54) VISCOELASTIC MODELING OF BLOOD VESSELS

(71) Applicants: Lucian Mihai Itu, Brasov (RO); Puneet Sharma, Monmouth Junction, NJ (US); Ali Kamen, Skillman, NJ (US); Dorin Comaniciu, Princeton Junction, NJ (US)

(72) Inventors: Lucian Mihai Itu, Brasov (RO); Puneet Sharma, Monmouth Junction, NJ (US); Ali Kamen, Skillman, NJ (US); Dorin Comaniciu, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 817 days.

(21) Appl. No.: 14/025,039

(22) Filed: Sep. 12, 2013

(65) Prior Publication Data
US 2014/0088935 A1   Mar. 27, 2014

Related U.S. Application Data

(60) Provisional application No. 61/704,733, filed on Sep. 24, 2012.

(51) Int. Cl.
| | |
|---|---|
| *G06F 19/00* | (2018.01) |
| *A61B 34/10* | (2016.01) |
| *G16H 50/50* | (2018.01) |
| *G06T 7/12* | (2017.01) |
| *A61B 5/026* | (2006.01) |
| *A61B 6/00* | (2006.01) |
| *A61B 5/00* | (2006.01) |
| *G16B 5/00* | (2019.01) |

(52) U.S. Cl.
CPC ............... *G16B 5/00* (2019.02); *G16H 50/50* (2018.01)

(58) Field of Classification Search
None
See application file for complete search history.

(56) References Cited

U.S. PATENT DOCUMENTS

| | | | | |
|---|---|---|---|---|
| 7,191,110 B1* | 3/2007 | Charbel | ................ | G06F 19/321 434/262 |
| 8,315,812 B2* | 11/2012 | Taylor | ................ | A61B 5/02007 382/128 |
| 2012/0022843 A1 | 1/2012 | Ionasec et al. | | |
| 2012/0053918 A1* | 3/2012 | Taylor | ................ | A61B 5/02007 703/9 |
| 2012/0203530 A1* | 8/2012 | Sharma | ................ | G06F 19/3437 703/9 |

FOREIGN PATENT DOCUMENTS

| | | |
|---|---|---|
| CN | 1559345 | 1/2005 |
| CN | 101529241 | 9/2009 |

OTHER PUBLICATIONS

Canic et al. (SIAM J. Applied Mathematics (2006) vol. 67:164-193).*
Luo (Journal of Newtonian Fluid Mechanics (1996) vol. 63, pp. 121-140).*
Raghu et al. (Journal of Biomechanical Eng. (2011) vol. 133:1-11).*
Liu, Xiaoheng et al. "Study on the Couple Motion Between Vessel Wall and Blood in the Entrance Region of Viscoelastic Vessels" Acta Biophysica Sinica, vol. 14, No. 2, Jun. 1998 pp. 353-359.
Zhao-Rong, Liu et al. "An Analysis Model of Pulsatile Blood Flow in Arteries" Applied Mathematics and Mechanics, 2003, pp. 205-216.
Zhiyong, Yin et al. "The 5-element Viscoelasticity Model of the Blood and the Physiological Signification" Journal of Chongqing University (Natural Science Edition) vol. 22, 1999, pp. 39-44.
Spilker, Ryan L. et al. "Morphometry-Based Impedance Boundary Conditions for Patient-Specific Modeling of Blood Flow in Pulmonary Arteries" Annals of Biomedical Engineering, vol. 35, No. 4, Apr. 2007, pp. 546-559.
J. Alastruey et al., "Pulse wave propagation in a model human arterial network: Assessment of 1-D visco-elastic simulations against in vitro measurements," Journal of Biomechanics, vol. 44, pp. 2250-2258, 2011.
T. Anor et al., "Modeling of Blood Flow in Arterial Trees, Wiley Interdisciplinary Reviews," Systems Biology and Medicine, vol. 2, pp. 612-623, 2010.
D. Bessems et al., "Experimental validation of a time-domain-based wave propagation model of blood flow in viscoelastic vessels," Journal of Biomechanics, vol. 41, pp. 284-291, 2008.
J. S. Coogan et al., "Computational fluid dynamic simulations of aortic coarctation comparing the effects of surgical and stent-based treatments on aortic compliance and ventricular workload," Catheter. Cardiov. Interv. vol. 77, pp. 680-691, 2011.
L. Formaggia et al., "One dimensional models for blood flow in arteries," Journal of Engineering Mathematics, vol. 47, pp. 251-276, 2003.
L. Formaggia et al., "Numerical Modeling of 1D Arterial Networks Coupled with a Lumped Parameters Description of the Heart," Computer Methods in Biomechanics and Biomedical Engineering, vol. 9, pp. 273-288, 2006.
Y. Fung, "Biomechanics: Mechanical properties of living tissues," 2nd edition, Springer-Verlag, New York, 1993; pp. 41-48.
R. Holenstein et al., "A Viscoelastic Model for Use in Predicting Arterial Pulse Waves," Journal of Biomechanical Engineering, vol. 102, pp. 318-325, 1980.

(Continued)

*Primary Examiner* — Lori A. Clow

(57) ABSTRACT

A method for modeling a blood vessel includes: (a) modeling a first segment of the blood vessel based on medical imaging data acquired from a subject; (b) computing a first modeling parameter at an interior point of the first segment; and (c) computing a second modeling parameter at a boundary point of the first segment using a viscoelastic wall model. Systems for modeling a blood vessel are described.

21 Claims, 24 Drawing Sheets

(56) References Cited

OTHER PUBLICATIONS

J. F. LaDisa, Jr. et al., "Computational Simulations for Aortic Coarctation: Representative Results From a Sampling of Patients," Journal of Biomechanical Engineering, vol. 133, pp. 091008-1-091008-9, 2011.

C. Malossi et al., "A two-level time step technique for the partitioned solution of one-dimensional arterial networks," Computer Methods in Applied Mechanics and Engineering, vol. 237-240, pp. 212-226, 2012.

J. P. Mynard et al., "A 1D arterial blood flow model incorporating ventricular pressure, aortic valve and regional coronary flow using the locally conservative Galerkin (LCG) method," Communications in Numerical Methods in Engineering, vol. 24, pp. 367-417, 2008.

M. Olufsen et al., "Numerical Simulation and Experimental Validation of Blood Flow in Arteries with Structured-Tree Outflow Conditions," Annals of Biomedical Engineering, vol. 28, pp. 1281-1299, 2000.

T. Passerini, "Computational hemodynamics of the cerebral circulation: multiscale modeling from the circle of Willis to cerebral aneurysms," PhD Thesis, Politecnico di Milano, Italy, 2009 127 pages annotated LAC Mar. 16, 2019.

T. Passerini et al., "A 3D/1D geometrical multiscale model of cerebral vasculature," Journal of Engineering Mathematics, vol. 64, pp. 319-330, 2009.

A. Quarteroni et al., "Computational Vascular Fluid Dynamics: Problems, Models and Methods," Computing and Visualization in Science, vol. 2, pp. 163-197, 2000.

P. Reymond et al., "Validation of a patient-specific one-dimensional model of the systemic arterial tree," American Journal of Physiology-Heart and Circulatory Physiology, vol. 301, pp. 1173-1182, 2011.

P. Segers et al., "Assessment of distributed arterial network models," Medical and Biological Engineering and Computing, vol. 35, pp. 729-736, 1997.

N. Stergiopulos et al., "Computer simulation of arterial flow with applications to arterial and aortic stenosis," Journal of Biomechanics, vol. 25, pp. 1477-1488, 1992.

C. A. Taylor et al., "Image-Based Modeling of Blood Flow and Vessel Wall Dynamics: Applications, Methods and Future Directions," Annals of Biomedical Engineering, vol. 38, pp. 1188-1203, 2010.

I. E. Vignon-Clementel et al., "Outflow boundary conditions for 3D simulations of non-periodic blood flow and pressure Fields in deformable arteries," Computer Methods in Biomechanics and Biomedical Engineering, vol. 13, pp. 625-640, 2010.

D. Valdez-Jasso et al., "Analysis of Viscoelastic Wall Properties in Ovine Arteries," IEEE Transactions on Biomedical Engineering, vol. 56, pp. 210-219, 2009.

H. K. Wesseling et al., "Estimated Five Component Viscoelastic Model Parameters for Human Arterial Walls," Journal of Biomechanics, vol. 6, pp. 13-24, 1973.

N. Westerhof et al., "Arterial Viscoelasticity: A Generalized Model: Effect on Input Impedance and Wave Travel in the Systematic Tree," Journal of Biomechanics, vol. 3, pp. 357-379, 1970.

\* cited by examiner

VISCOELASTIC MODELING OF BLOOD VESSELS

RELATED APPLICATIONS

This application claims the benefit of U.S. Provisional Application No. 61/704,733, filed Sep. 24, 2012. The entire contents of the provisional application are incorporated herein by reference, except that in the event of any inconsistent disclosure or definition from the present specification, the disclosure or definition herein shall be deemed to prevail.

TECHNICAL FIELD

The present teachings relate generally to blood flow modeling and, more particularly, to blood flow modeling that takes into account viscoelasticity.

BACKGROUND

Cardiac disease is the leading cause of death for men and women in the United States and accounts for at least 30% of deaths worldwide. Although recent medical advances have resulted in improvements in the diagnosis and treatment of complex cardiac diseases, the incidence of premature morbidity and mortality remains large, at least in part due to a dearth of accurate in vivo and in vitro estimates of patient-specific parameters indicative of a patient's anatomy, physiology, and hemodynamics.

Blood flow modeling of the cardiovascular system provides insight into the conditions in a patient's blood vessels and may be useful for diagnostics, prognosis, and surgical planning. Models with different geometrical scales have been applied, including lumped models (e.g., 0D-models), one-dimensional models, and three-dimensional models with rigid or compliant walls (e.g., fluid-structure interaction models). Lumped models may be used to obtain quick results but are unable to capture wave propagation phenomena in an arterial tree. Three-dimensional models, on the other hand, may accurately model the local behavior of blood, but are computationally very expensive, thus making the modeling of complex arterial trees infeasible in a clinical setting. The one-dimensional model represents a good balance between computational speed and accuracy.

SUMMARY

The scope of the present invention is defined solely by the appended claims, and is not affected to any degree by the statements within this summary.

The present teachings may be used to model arterial blood flow networks based on a viscoelastic model of the artery. In some embodiments, the viscoelastic problem may be solved for the individual blood vessel segments, and a coupling algorithm that takes viscoelasticity into account at the boundary points of the individual segments (e.g., inlets, outlets, and junctions) may be used to couple the individual segments.

A computer-implemented method for modeling a blood vessel in accordance with the present teachings includes: (a) modeling, by a processor, a first segment of the blood vessel based on medical imaging data acquired from a subject; (b) computing, by the processor, a first modeling parameter at an interior point of the first segment; and (c) computing, by the processor, a second modeling parameter at a boundary point of the first segment using a viscoelastic wall model.

A system for modeling a blood vessel in accordance with the present teachings includes: (a) a processor; (b) a non-transitory memory coupled with the processor; (c) first logic stored in the non-transitory memory and executable by the processor to cause the processor to model a first segment of the blood vessel based on medical imaging data acquired from a subject; (d) second logic stored in the non-transitory memory and executable by the processor to cause the processor to compute a first modeling parameter at an interior point of the first segment; and (e) third logic stored in the non-transitory memory and executable by the processor to cause the processor to compute a second modeling parameter at a boundary point of the first segment using a viscoelastic wall model.

A non-transitory computer readable storage medium in accordance with the present teachings has stored therein data representing instructions executable by a programmed processor for modeling a blood vessel. The storage medium includes instructions for (a) modeling a first segment of the blood vessel based on medical imaging data acquired from a subject; (b) computing a first modeling parameter at an interior point of the first segment; and (c) computing a second modeling parameter at a boundary point of the first segment using a viscoelastic wall model.

BRIEF DESCRIPTION OF THE DRAWINGS

FIG. 10 shows plots of time-varying pressure, time-varying flow rate, and time-varying cross-sectional area comparing a bifurcation test case obtained with an elastic model to the models V1, V2, V1-int, and V2-int. Data for the parent vessel are shown in (a), data for the daughter 1 vessel are shown in (b), and data for the daughter 2 vessel are shown in (c).

DETAILED DESCRIPTION

Figure 1:
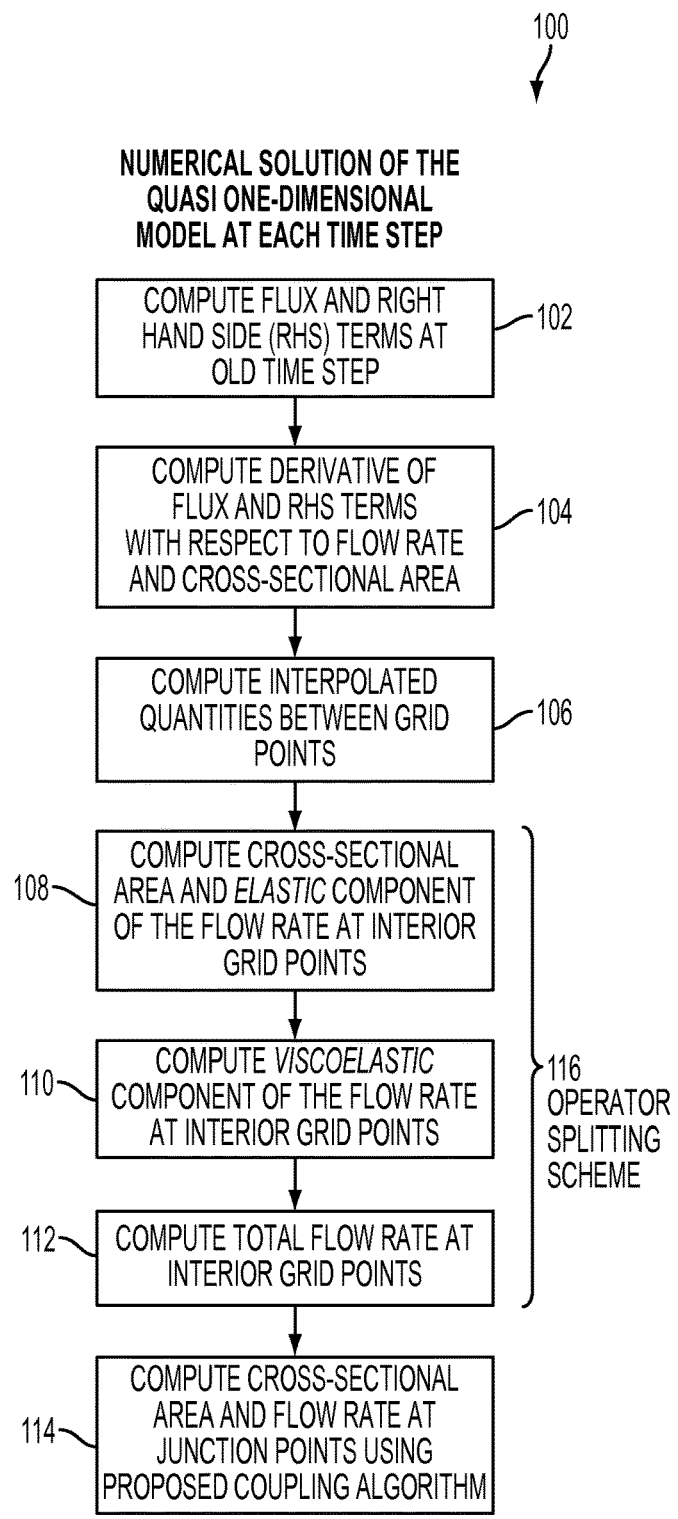
FIG. 1 shows a flow chart of an exemplary method for numerical implementation using a viscoelastic wall model.

Blood flow modeling in accordance with the present teachings is based on a viscoelastic wall model coupled with computational fluid dynamics (CFD)-based blood flow calculations. Coupling algorithms in accordance with the present teachings take into consideration the effect of viscoelasticity at boundary points of blood vessels (e.g., inflow points, outflow points, and junction points) in order to improve accuracy in modeling physiological processes.

In some embodiments, a coupling algorithm in accordance with the present teachings facilitates computation of the time-varying pressure and cross-sectional area values when an operator-splitting scheme is used for the numerical solution of a viscoelastic quasi one-dimensional model. In some embodiments, the numerical solution of the viscoelastic quasi one-dimensional model recovers the original hyperbolic nature of a one-dimensional model (e.g., allows for an explicit solution scheme and, therefore, short execution times). In some embodiments, the coupling algorithm may be used for all manner of multi-scale domain coupling (e.g., 3-D domains, 1-D domains, and 0-D domains). In some embodiments, by being iterative, the coupling algorithm provides strong coupling between upstream and downstream domains of which there may be many in a single junction. In some embodiments, the numerical solution facilitates computation of a hysteresis loop in a pressure-area relationship that characterizes an energy loss stemming from viscous behavior of the arterial wall. In some embodiments, the coupling algorithm may be applied for different viscoelastic wall models (e.g., different Voigt-type materials).

It is to be understood that elements and features of the various representative embodiments described below may be combined in different ways to produce new embodiments that likewise fall within the scope of the present teachings.

By way of general introduction, a method for modeling a blood vessel in accordance with the present teachings includes: (a) modeling a first segment of the blood vessel based on medical imaging data acquired from a subject; (b) computing a first modeling parameter at an interior point of the first segment; and (c) computing a second modeling parameter at a boundary point of the first segment using a viscoelastic wall model.

In some embodiments, a method in accordance with the present teachings further includes one or a plurality of the following additional acts: (d) implementing an operator-splitting scheme; and/or (e) coupling a first domain of the first segment of the blood vessel to a second domain of a second segment of the blood vessel, wherein the first domain includes the boundary point.

In some embodiments, a method for modeling a blood vessel in accordance with the present teachings is implemented using a computer and, in some embodiments, one or a plurality of the acts of (a) modeling, (b) computing, (c) computing, (d) implementing, and/or (e) coupling described above are performed by one or a plurality of processors.

In some embodiments, a model obtained by the modeling comprises a zero-dimensional model, a one-dimensional model, a three-dimensional model, or a combination thereof. In some embodiments, the model comprises a one-dimensional model.

Methods in accordance with the present teachings are independent of the type of medical imaging data that is used to model a blood vessel. All manner of medical imaging modalities that are capable of providing anatomical information sufficient to initiate a domain are contemplated for use in accordance with the present teachings. Representative medical imaging data include but are not limited to magnetic resonance data, computed tomography data, positron emission tomography data, single photon emission tomography data, ultrasound data, angiographic data, x-ray data, and the like, and combinations thereof. The medical imaging data may represent part of an interior region of a patient.

Computations of modeling parameters at boundary points of blood vessel segments (e.g., inlets, outlets, and junctions) may be performed using a viscoelastic wall model. In some embodiments, computations of modeling parameters at interior points of the blood vessel segments may also use a viscoelastic wall model, which may be the same as or different than the viscoelastic wall model used at the boundary points.

In some embodiments, the first modeling parameter is a cross-sectional area, an elastic component of a flow rate, a viscoelastic component of the flow rate, a total flow rate, or combinations thereof. In some embodiments, the second modeling parameter is a cross-sectional area, a flow rate, or a combination thereof.

As used herein, the phrase "boundary point" refers to a non-interior point of a blood vessel, including but not limited to inflow points (inlets), outflow points (outlets), and junction points (e.g., bifurcations, trifurcations, quadfurcations, pentafurcations, hexafurcations, and the like, and combinations thereof).

For embodiments that include the act (e) of coupling a first domain of the first segment of the blood vessel to a second domain of a second segment of the blood vessel, wherein the first domain includes the boundary point, a geometrical scale of the first domain may be different than a geometrical scale of the second domain. For example, a main domain of interest may be solved as a 3-D model, whereas the inlet and outlet conditions may be solved as a 1-D model or a 0-D model.

FIG. 1 shows a flowchart of an exemplary method 100 for numerical implementation using a viscoelastic wall model. At block 102, flux and right hand side (RHS) terms are computed at an old time step. The derivative of flux and RHS terms is computed with respect to flow rate and cross-sectional area at block 104. At block 106, interpolated quantities between grid points are computed. Blocks 108, 110, and 112 together form an operator-splitting scheme 116. At block 108, cross-sectional area and an elastic component of flow rate at interior grid points are computed. At block 110, a viscoelastic component of the flow rate at interior grid points is computed. At block 112, total flow rate at interior grid points is computed. At block 114, cross-sectional area and flow rate at junction points are computed using a coupling algorithm in accordance with the present teachings.

Figure 2:
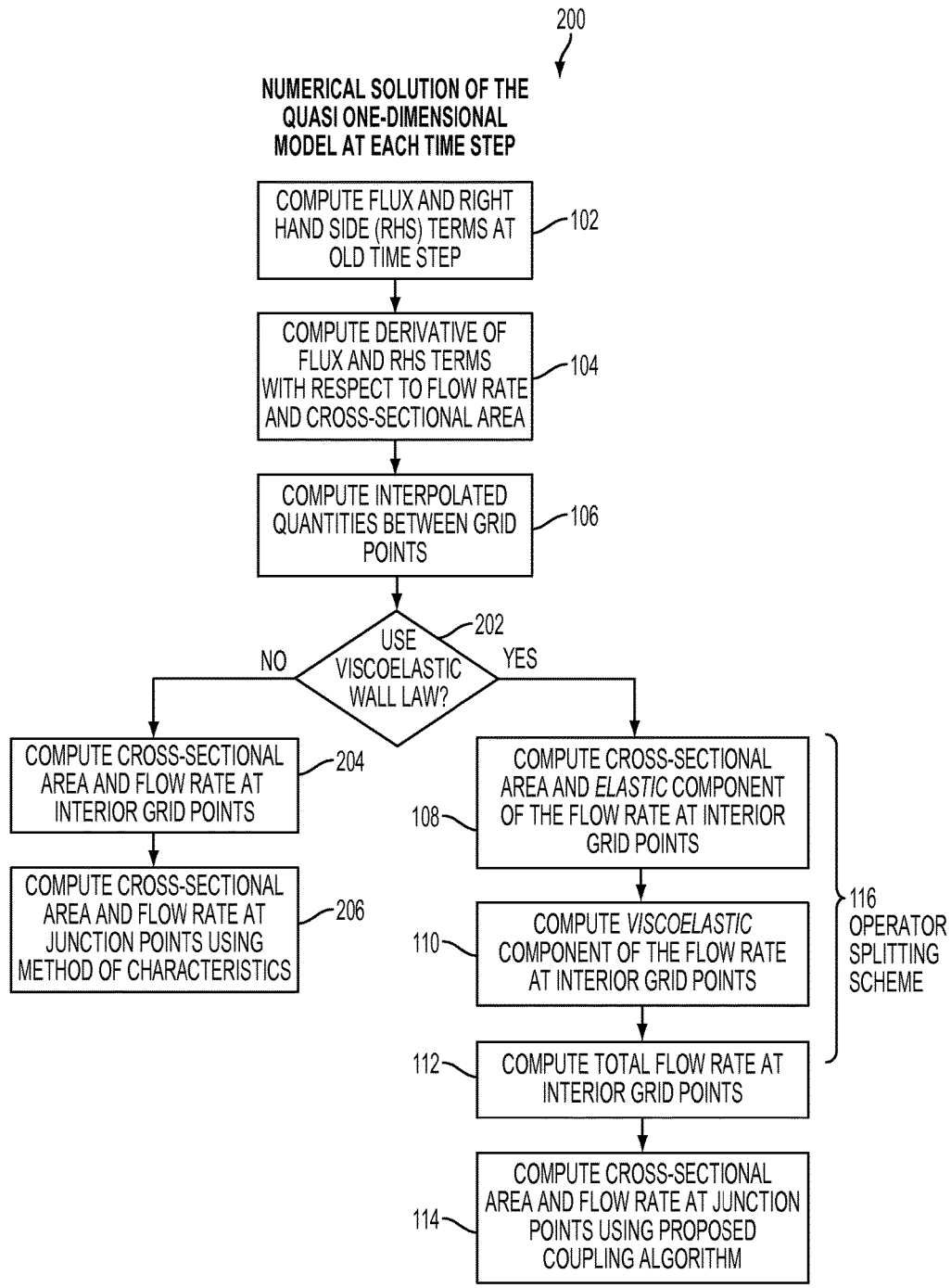
FIG. 2 shows a flow chart of an exemplary method for numerical implementation using an elastic/viscoelastic wall model.

FIG. 2 shows a flow chart of an exemplary method 200 for numerical implementation using an elastic/viscoelastic wall model. In FIGS. 1 and 2, like reference numerals designate corresponding elements. Each of FIGS. 1 and 2 includes an operator-splitting scheme 116 as described above for the numerical solution of a viscoelastic quasi one-dimensional model. At decision block 202 of FIG. 2, if a viscoelastic wall model is to be used, the process may proceed to block 108. If not, the process proceeds to block 204 at which cross-sectional area and flow rate are computed at interior grid points. At block 206, cross-sectional area and flow rate at junction points are computed using a method of characteristics. In some embodiments, the computing of the first modeling parameter at an interior point of a blood vessel in accordance with the present teachings includes an operator-splitting scheme 116 of a type shown in FIGS. 1 and 2. In some embodiments, the computing of the first modeling parameter includes computing a cross-sectional area at the interior point, computing an elastic component of a flow rate at the interior point, computing a viscoelastic component of the flow rate at the interior point, and computing a total flow rate at the interior point, as shown in the grouping 116 of acts 108, 110, and 112 in FIGS. 1 and 2.

In some embodiments, the computing of the second modeling parameter at the boundary point includes computing a cross-sectional area at the boundary point, and computing a flow rate at the boundary point, as shown, for example, at block 114 of FIGS. 1 and 2.

Figure 3:
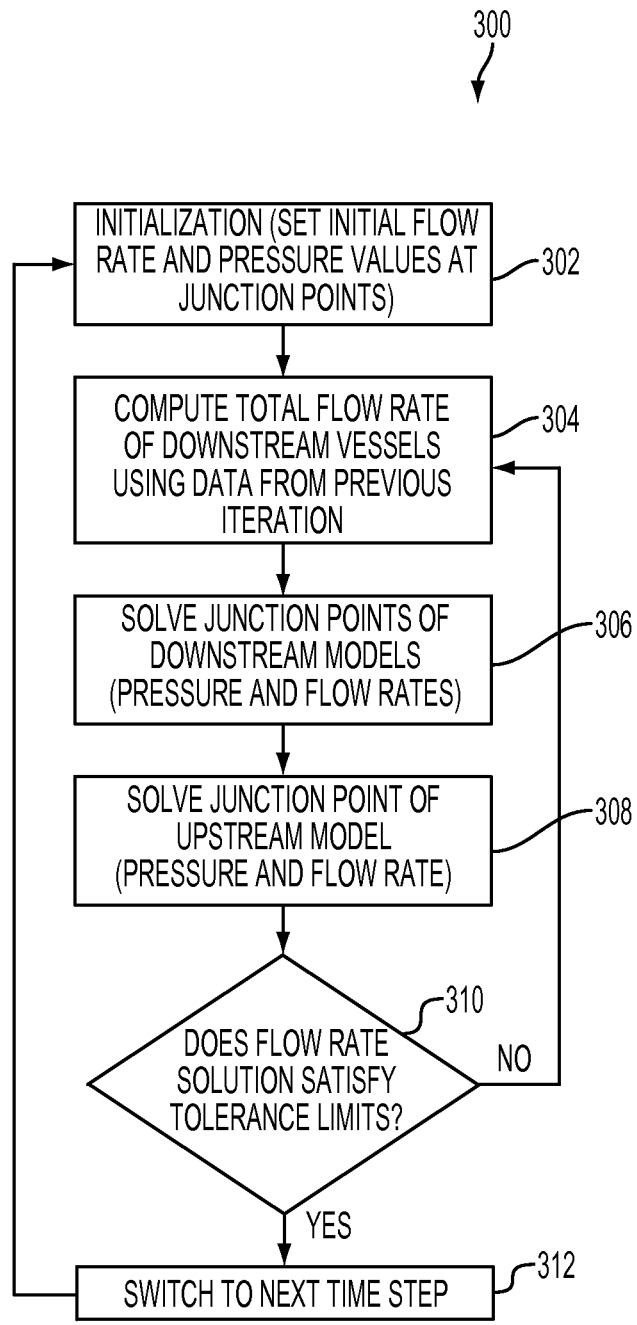
FIG. 3 shows a flow chart of an exemplary coupling algorithm.

FIG. 3 shows a flow chart of an exemplary coupling algorithm 300 for use in accordance with the present teachings. As shown in FIG. 3, initialization occurs at block 302, at which initial flow rate and pressure values are set at junction points. At block 304, total flow rate of downstream vessels is computed using data from a previous iteration. At block 306, junction points of downstream models (e.g., pressure and flow rates) are solved. At block 308, junction points of upstream models (e.g., pressure and flow rates) are solved. At decision block 310, if the flow rate solution satisfies tolerance limits, the algorithm may proceed to block 312 and switch to the next time step. Otherwise, the process returns to block 304.

Figure 4:
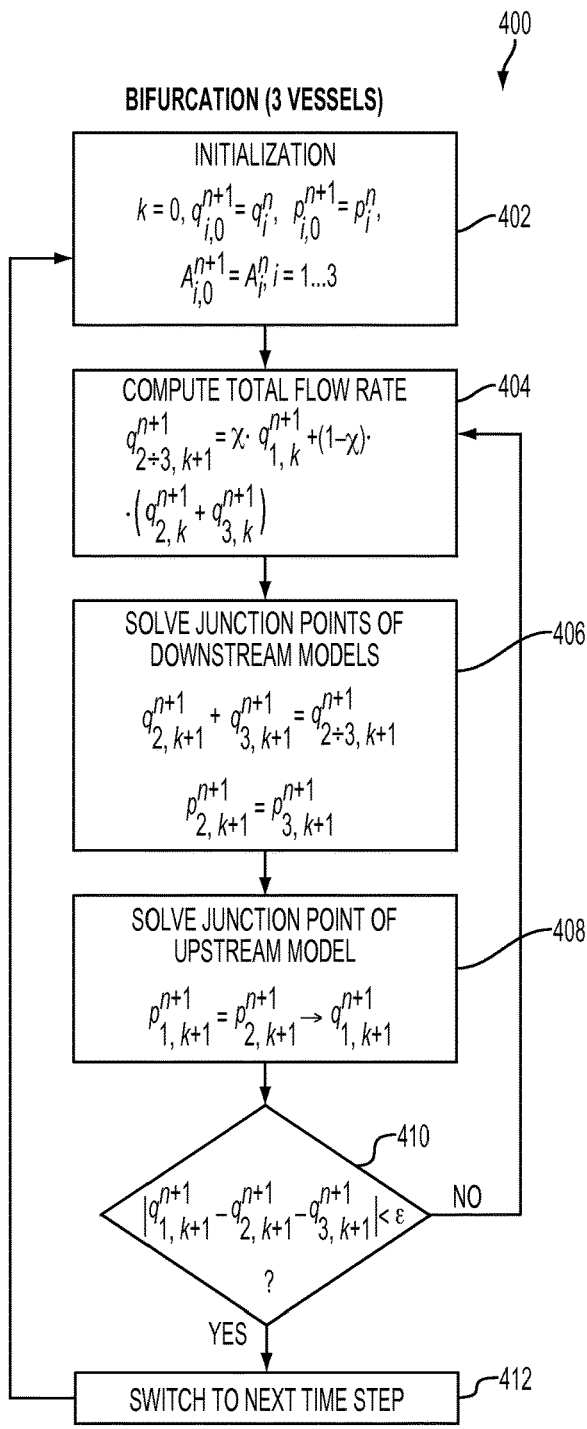
FIG. 4 shows a flowchart illustrating an exemplary coupling technique for a bifurcation.

FIG. 4 shows a flowchart (with equations) that illustrates an exemplary coupling technique 400 for a bifurcation (e.g., three vessels). As shown in FIG. 4, initialization occurs at block 402, total flow rate is computed at block 404, junction points of downstream models are solved at block 406, and junction points of upstream models are solved at block 408. If the criterion in decision block 410 is satisfied, the process may proceed to block 412 and switch to the next time step. Otherwise, the process returns to block 404.

Figure 5:
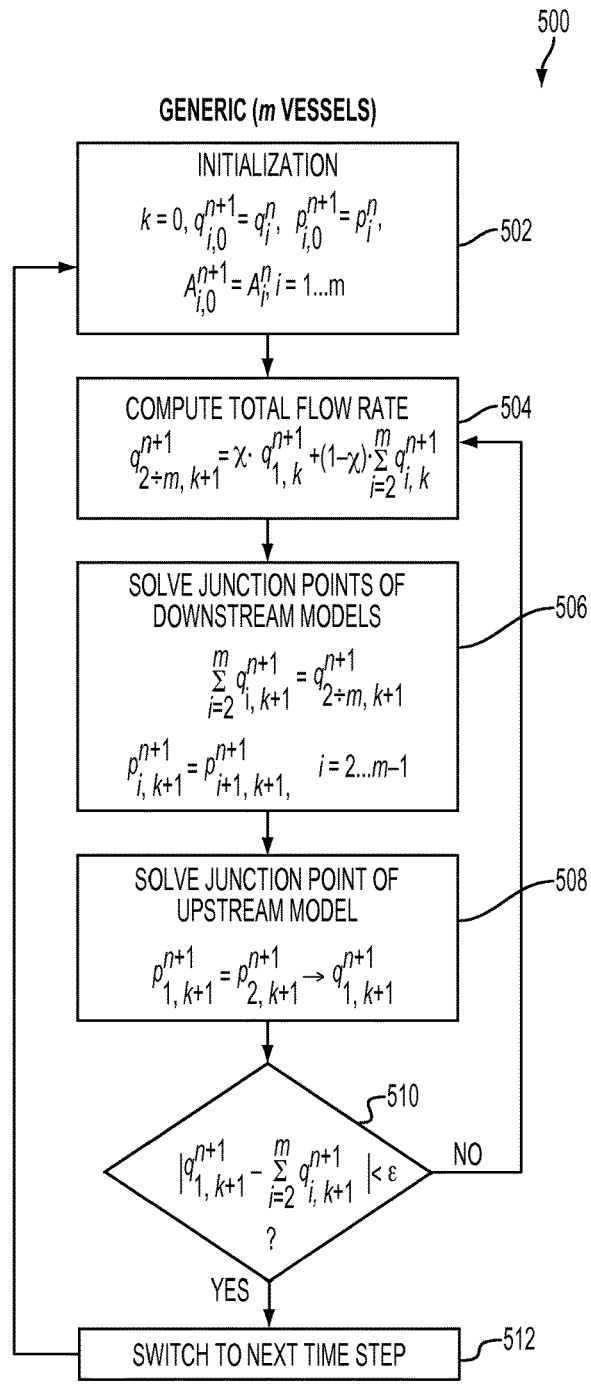
FIG. 5 shows a flowchart illustrating an exemplary coupling technique for a generic junction with m vessels.

FIG. 5 shows a flowchart (with equations) analogous to that shown in FIG. 4 that illustrates an exemplary coupling technique 500 for a generic junction with m vessels. As shown in FIG. 5, initialization occurs at block 502, total flow rate is computed at block 54, junction points of downstream models are solved at block 506, and junction points of upstream models are solved at block 508. If the criterion in decision block 510 is satisfied, the process may proceed to block 512 and switch to the next time step. Otherwise, the process returns to block 504.

In some embodiments, as described above, the present teachings provide methods for modeling a blood vessel. In other embodiments, as further described below, the present teachings also provide systems for modeling a blood vessel.

By way of example, a first system for modeling a blood vessel in accordance with the present teachings includes a processor coupled to a non-transitory memory, wherein the processor is operative to execute computer program instructions to cause the processor to: (a) model a first segment of the blood vessel based on medical imaging data acquired from a subject; (b) compute a first modeling parameter at an interior point of the first segment; and (c) compute a second modeling parameter at a boundary point of the first segment using a viscoelastic wall model.

Figure 6:
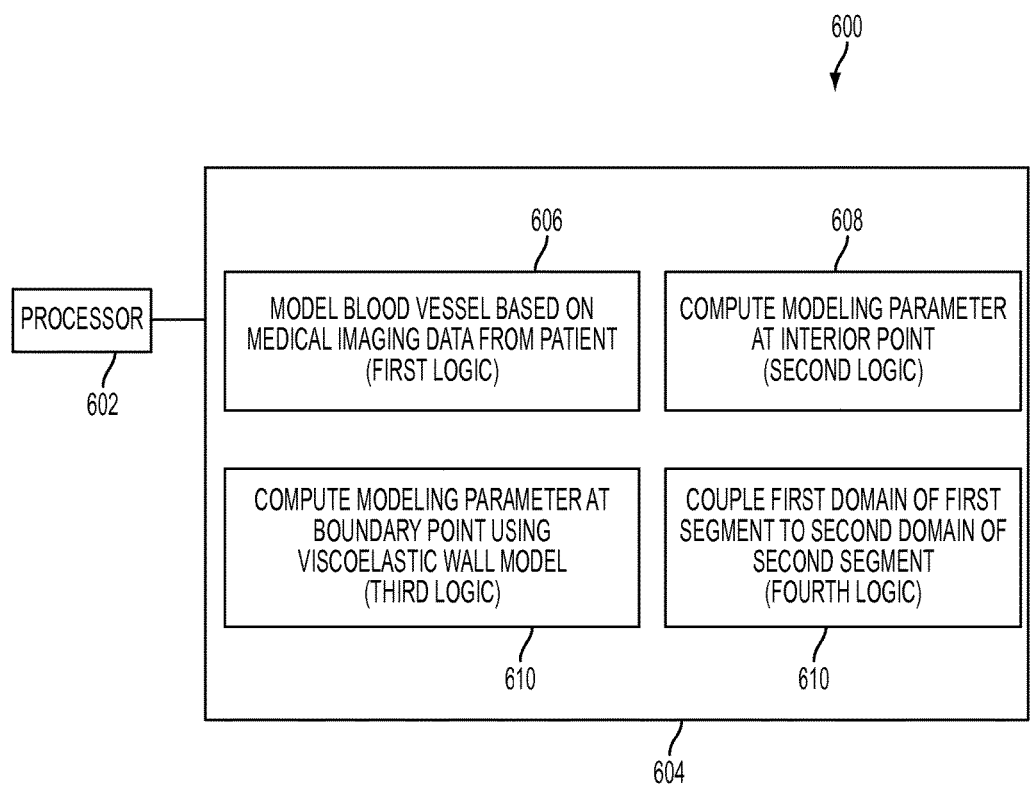
FIG. 6 shows a block diagram of an exemplary system 600 for modeling a blood vessel.
Figure 7:
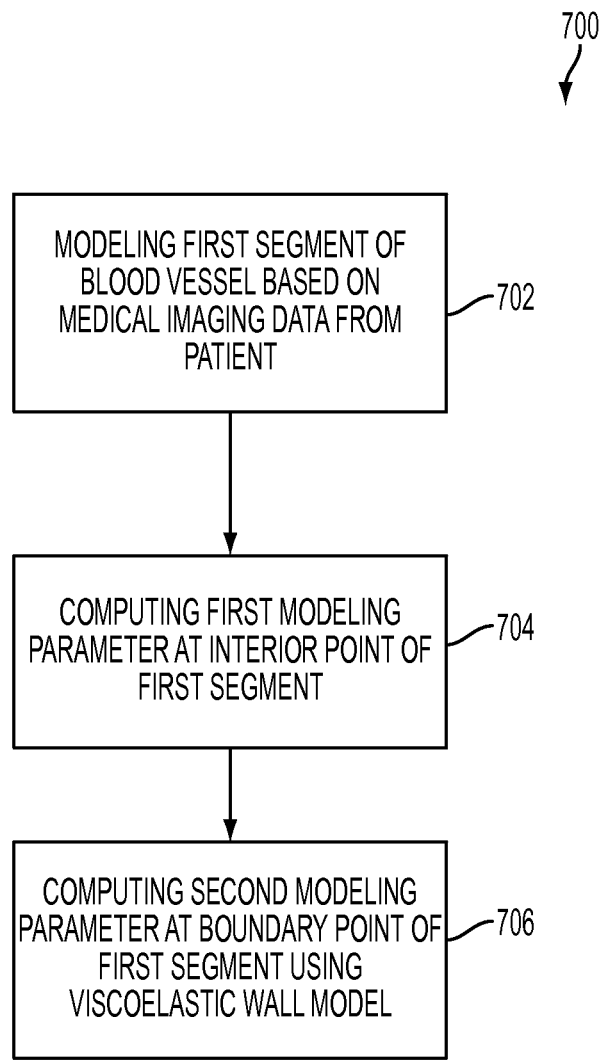
FIG. 7 shows a flow chart of an exemplary process 700 for modeling a blood vessel.

Further aspects of the present teachings will now be described in reference to FIGS. 6 and 7. FIG. 6 shows a block diagram of a representative system 600 for modeling a blood vessel in accordance with the present teachings. FIG. 7 depicts a flow chart showing exemplary operation of the representative system for modeling a blood vessel shown in FIG. 6.

In some embodiments, as shown in FIG. 6, a system 600 for modeling a blood vessel in accordance with the present teachings is implemented as part of a modeling module in a computer system. As shown in FIG. 1, the system 600 includes: a processor 602; a non-transitory memory 604 coupled with the processor 602; first logic 606 stored in the non-transitory memory 604 and executable by the processor 602 to cause the processor 602 to model a first segment of the blood vessel based on medical imaging data acquired from a subject; second logic 608 stored in the non-transitory memory 604 and executable by the processor 602 to cause the processor 602 to compute a first modeling parameter at an interior point of the first segment; third logic 610 stored in the non-transitory memory 604 and executable by the processor 602 to cause the processor 602 to compute a second modeling parameter at a boundary point of the first segment using a viscoelastic wall model; and fourth logic 612 stored in the non-transitory memory 604 and executable by the processor 602 to cause the processor 602 to couple a first domain of the first segment of the blood vessel to a second domain of a second segment of the blood vessel, wherein the first domain includes the boundary point.

In some embodiments, the system 600 may be coupled to other modules of a computer system and/or to databases so as to have access to relevant information as needed (e.g., medical imaging data, patient identification data, etc.) and initiate appropriate actions.

FIG. 7 depicts a flow chart showing exemplary operation of the system 600 of FIG. 6. In particular, FIG. 7 shows a computer-implemented method 700 for modeling a blood vessel in accordance with the present teachings that includes: (a) modeling 702, by a processor, a first segment of the blood vessel based on medical imaging data acquired from a subject; (b) computing 704, by the processor, a first modeling parameter at an interior point of the first segment; and (c) computing 706, by the processor, a second modeling parameter at a boundary point of the first segment using a viscoelastic wall model.

The relative ordering of some acts shown in the flow chart of FIG. 7 is meant to be merely representative rather than limiting, and that alternative sequences may be followed. Moreover, additional, different, or fewer acts may be provided, and two or more of these acts may occur sequentially, substantially contemporaneously, and/or in alternative orders. By way of a non-limiting and representative example, in FIG. 7, the act of computing 704 a first modeling parameter at an interior point of the first segment is shown as preceding the act of computing 706 a second modeling parameter at a boundary point of the first segment using a viscoelastic wall model. However, in alternative embodiments, act 706 may precede act 704.

A further system for modeling a blood vessel includes: means for modeling a first segment of the blood vessel based on medical imaging data acquired from a subject; means for computing a first modeling parameter at an interior point of the first segment; and means for computing a second modeling parameter at a boundary point of the first segment using a viscoelastic wall model.

A non-transitory computer-readable storage medium in accordance with the present teachings has stored therein data representing instructions executable by a programmed processor for modeling a blood vessel. The storage medium includes instructions for: (a) modeling a first segment of the blood vessel based on medical imaging data acquired from a subject; (b) computing a first modeling parameter at an interior point of the first segment; and (c) computing a second modeling parameter at a boundary point of the first segment using a viscoelastic wall model.

Multi-scale models model local blood flow patterns by using a three-dimensional model for a region of interest and reduced-order models (e.g., 1-D, 0-D) to account for the influence of the rest of the circulation on a region of interest.

One-dimensional models may be used to accurately predict time-varying flow rate and pressure waveforms for patient-specific models. While most one-dimensional models described in the literature use elastic wall models, the arterial wall is actually a viscoelastic material. Thus, a phase shift occurs between pressure and area and leads to a hysteresis curve in the pressure-area relationship. In addition to the phase shift between area and pressure, the viscoelastic properties of the wall dampen high frequency oscillations for both the pressure and the flow rate waveform, as has been shown for an in vitro model. The use of a viscoelastic wall model in a full-body circulation model has led to similar conclusions. In both cases, no results have been reported for the time-dependent variation of the cross-sectional area.

Several viscoelastic wall models have been introduced in the literature independently of one-dimensional blood flow models. The parameters in the models are obtained from experiments. By way of example, a viscoelastic wall model used in a linear 1-D blood flow model shows that the pressure pulse increase towards distal vessel is reduced. Further, the differences in pressures between the elastic wall model and the viscoelastic wall model were smaller than 4 mmHg. Different viscoelastic models have led to similar results.

In connection with non-linear one-dimensional models, the results obtained with viscoelastic models may be closer to in vivo measurements than results obtained with elastic models. One study that uses a whole body circulation model has shown that the effects of viscoelasticity are greater in the peripheral vessels. Overall, the introduction of viscoelasticity has led to a change of up to 4% for pressure and 2.3% for flow rate. Another study comparing two different viscoelastic models for an abdominal aorta model indicates that the viscoelastic term primarily influences cross-sectional area variation.

For a one-dimensional blood flow model that uses an elastic wall model, a hyperbolic system of equations is obtained that may be solved using the first-order method of characteristics or the second-order Lax-Wendroff method. When a viscoelastic wall model is used instead, the hyperbolic nature of the equations is lost due to the additional term(s) in the pressure-area relationship. In this case, the approaches for the numerical solution of the equations may be divided into two main categories: first, methods that do not exploit the original hyperbolic nature of the equations (e.g., a discontinuous finite element Galerkin method with stabilization terms; an implicit finite difference/spectral element method wherein non-linear terms are solved iteratively at each time-step using the Newton-Raphson method; etc.); and second, methods that recover the original hyperbolic nature of the equations by employing an operator-splitting scheme for the momentum equation.

The second method is computationally faster than the first method since the second method exploits the hyperbolic nature of the mass conservation and modified momentum conservation equations. However, the second method introduces an approximation through the operator-splitting approach. Apparently contradictory results have been obtained by using the first method and the second method. One study using a model of the abdominal aorta has shown that the pressure waveform is largely unaffected by the viscoelastic term although a smaller cross-sectional area variation is obtained. Another study reports a higher-pressure pulse when viscoelasticity is added. A potential cause of the contradictory conclusions described above is a neglect of the viscoelastic term at the boundary grid points of each vessel segment (e.g., inflow, junction, outflow).

A method in accordance with the present teachings uses an operator-splitting scheme for the numerical solution of the viscoelastic term. In order to include the viscoelastic term at the inlet and outlet boundaries of each vessel segment, a coupling method may be used.

The one-dimensional blood flow model may be obtained from the three-dimensional Navier-Stokes equations based on a series of simplifying assumptions and includes the mass conservation and momentum conservation equations:

$$\frac{\partial A(x,t)}{\partial t} + \frac{\partial q(x,t)}{\partial x} = 0, \quad (1)$$

$$\frac{\partial q(x,t)}{\partial t} + \frac{\partial}{\partial x}\left(\alpha \frac{q^2(x,t)}{A(x,t)}\right) + \frac{A(x,t)}{\rho}\frac{\partial p(x,t)}{\partial x} = K_R \frac{q(x,t)}{A(x,t)}, \quad (2)$$

wherein $A(x,t)$ represents cross-sectional area, $p(x,t)$ represents pressure, and $q(x,t)$ represents flow rate. In EQN. (2), $\alpha$ represents the momentum-flux correction coefficient and $K_R$ represents a friction parameter to account for the viscous losses. In the description that follows, a parabolic velocity profile will be used, such that $K_R = -8\pi\nu$ and $\alpha = 4/3$, wherein $\nu$ represents the kinematic viscosity.

In order to close the system, a state equation that relates the pressure inside the vessels to the cross-sectional area may be used. The vessel wall may be modeled as a purely elastic material.

$$p(x,t) = \Psi_{el}(A) + p_0 = \frac{4}{3}\frac{Eh}{r_0}(x)\left(1 - \sqrt{\frac{A_0(x)}{A(x,t)}}\right) + p_0, \quad (3)$$

wherein E is the Young modulus, h is the wall thickness, and $r_0$ is the initial radius corresponding to the initial pressure $p_0$.

The elastic wall properties may be estimated using a best fit to experimental data:

$$\frac{Eh}{r_0}(x) = k_1 \cdot \exp(k_2 \cdot r_0(x)) + k_3$$

wherein:

$k_1 = 2 \cdot 10^7$ g/($s^2$·cm), $k_2 = -22.53$ cm$^{-1}$, $k_3 = 4.65 \cdot 10^5$ g/($s^2$·cm).

Other properties may be used.

In order to simplify the expressions, the spatial and temporal dependencies of the quantities may be omitted.

Bifurcations may be solved by considering the continuity of flow and total pressure:

$$q_p = \sum_i (q_d)_i, \quad (4)$$

$$p_p + \frac{1}{2}\rho\frac{q_p^2}{A_p^2} = (p_d)_i + \frac{1}{2}\rho\frac{(q_d^2)_i}{(A_d^2)_i}, \quad (5)$$

wherein the subscript p refers to the parent vessel and the subscript d refers to the daughter vessels.

Proper boundary conditions may be specified at the inlet and the outlets of the computational domain. Depending on the availability of in vivo measurements and the underlying assumptions used in the modeling, (i) a time-varying flow rate profile or (ii) a lumped model of the heart coupled at the inlet may be used as an inlet boundary condition. A time-varying velocity profile (or flow rate profile) may be determined in a clinical setting, and form part of a diagnostic workflow (e.g., 2-D/3-D phase-contrast MRI, Doppler ultrasound).

For the outlet boundary condition, physiologically motivated three-element Windkessel boundary conditions may be used:

$$\frac{\partial p}{\partial t} = R_p \frac{\partial q}{\partial t} - \frac{p}{R_d \cdot C} + \frac{q(R_p + R_d)}{R_d \cdot C}. \tag{6}$$

The explicit Lax-Wendroff method (based on the expansion in Taylor series) may be used for the numerical implementation of hyperbolic equations. This method may result in short computational times, and is second order accurate in both time and space.

In the Lax-Wendroff method, equations are written in conservation form:

$$\frac{\partial U}{\partial t} + \frac{\partial R}{\partial x} = S, \tag{7}$$

$$U = \begin{pmatrix} A \\ q \end{pmatrix} \; R = \begin{pmatrix} R_1 \\ R_2 \end{pmatrix} = \begin{pmatrix} q \\ \alpha \frac{q^2}{A} + B \end{pmatrix} \tag{8}$$

$$S = \begin{pmatrix} S_1 \\ S_2 \end{pmatrix} = \begin{pmatrix} 0 \\ -K_R \frac{q}{A} + \frac{\partial B}{\partial r_0} \frac{dr_0}{dx} \end{pmatrix},$$

$$B(r_0(x), p(x,t)) = \frac{1}{\rho} \int_{p_0}^{p(x,t)} \Psi_{el}^{-1}(p') dp',$$

wherein U is the vector of the unknown quantities, R is the flux term, and S is the right hand side (RHS).

Equation (7) may be discretized in time as follows:

$$\frac{U^{n+1} - U^n}{\Delta t} = S^n - \frac{\partial R^n}{\partial x} - \frac{\Delta t}{2} \left[ \frac{\partial}{\partial x} \left( R_U^n S^n - R_U^n \frac{\partial R^n}{\partial x} \right) - S_U^n \frac{\partial R^n}{\partial x} - S_U^n S^n \right] \tag{9}$$

wherein all spatial derivatives are discretized using central difference schemes, and:

$$R_U^n = \frac{\partial R}{\partial U}; \; S_U^n = \frac{\partial S}{\partial U}. \tag{10}$$

For bifurcations and for outflows, the method of characteristics may be used to couple different one-dimensional domains, and respectively EQN. (6) to the one-dimensional equations. A locally first-order method results but the overall second-order character of the scheme is maintained.

In order to include viscoelasticity, the vessel wall may be considered a Voigt-type material. The tensile stress depends on both the tensile strain and the time-derivative of the strain. Thus, in order to analyze the effect of viscoelasticity, the following two state equations may be considered:

$$p(x,t) = \tag{11}$$

$$\Psi_{el}(A) + \Psi_v(A) + p_0 = \frac{4}{3} \frac{Eh}{r_0} \left( 1 - \sqrt{\frac{A_0}{A(x,t)}} \right) + \frac{\gamma_S}{A\sqrt{A}} \frac{\partial A}{\partial t} + p_0,$$

$$p(x,t) = \tag{12}$$

$$\Psi_{el}(A) + \Psi_v(A) + p_0 = \frac{4}{3} \frac{Eh}{r_0} \left( 1 - \sqrt{\frac{A_0}{A(x,t)}} \right) + \frac{\gamma_S}{A_0\sqrt{A}} \frac{\partial A}{\partial t} + p_0,$$

The difference between EQNS. (11) and (12) lies in the presence of either A or $A_0$ in the denominator of the viscoelastic term. In the description that follows, EQNS. (11) and (12) will be referred to as viscoelastic model V1 and V2, respectively. In order to perform an adequate comparison, the viscoelastic coefficient $\gamma_S$ is taken to be equal in both cases:

$$\gamma_S = \frac{T_S \cdot \tan \Phi_S}{4\pi} \frac{hE}{1-\sigma^2}, \tag{13}$$

wherein $T_S$ is the wave characteristic time, $\Phi_S$ is the viscoelastic angle, and $\sigma$ is the Poisson ratio. Similarly to an elastic wall coefficient, the viscoelastic coefficient is allowed to vary in space ($\gamma_S = \gamma_S(x)$).

The presence of a viscoelastic component in EQNS. (11) and (12) introduces an additional term in the momentum conservation equation:

$$\frac{\partial q}{\partial t} + \frac{\partial}{\partial x}\left(\alpha \frac{q^2}{A}\right) + \frac{A}{\rho} \frac{\partial \Psi_{el}}{\partial x} + \frac{A}{\rho} \frac{\partial \Psi_v}{\partial x} = K_R \frac{q}{A}. \tag{14}$$

Using the mass conservation equations, the viscoelastic term may be expressed as:

$$\Psi_v(x,t) = -\gamma \frac{\partial q}{\partial x}, \; \gamma = \frac{\gamma_S}{A_0 \sqrt{A}} \text{ or } \gamma = \frac{\gamma_S}{A\sqrt{A}}. \tag{15}$$

Thus, EQN. (14) may be rewritten as:

$$\frac{\partial q}{\partial t} + \frac{\partial R_2}{\partial x} - \frac{A}{\rho} \frac{\partial}{\partial x}\left(\gamma \frac{\partial q}{\partial x}\right) = S_2. \tag{16}$$

EQN. (16) is no longer hyperbolic and may not be cast into conservation form. In order to solve the system of equations using the conservation form, an operator-splitting scheme may be introduced. Such a scheme may be developed based on the assumption that the contribution of the viscoelastic term is of lesser importance than the elastic term. The flow rate is considered to be composed of an elastic component and a viscoelastic component ($q = q_e + q_v$), and EQN. (16) may be split into two equations:

$$\frac{\partial q_e}{\partial t} + \frac{\partial R_2}{\partial x} = S_2, \tag{17}$$

$$\frac{\partial q_v}{\partial t} - \frac{A}{\rho} \frac{\partial}{\partial x}\left(\gamma \frac{\partial q}{\partial x}\right) = 0. \tag{18}$$

The numerical solution at each stage is composed of two sequential stages. First, the system of equations (7) is solved using the Lax-Wendroff scheme to yield the quantities A(x,t) and $q_e$(x,t). In the second stage, EQN. (18) is solved to obtain $q_v(x,t)$ and, therefore, the total flow rate $q(x,t)$. EQN. (18) is discretized using central difference formulae resulting in a tridiagonal system of equations that may be solved using the Thomas algorithm. For the viscoelastic component of the flow, homogeneous Dirichlet boundary conditions may be imposed at the boundaries of each vessel.

In prior studies, the viscoelastic component of pressure has been neglected at bifurcations and outflow points. In order to assess the validity of this simplifying assumption, an iterative coupling algorithm in accordance with the present teachings may be applied equally to inflow points, bifurcation points, and outflow points. The algorithm is based on an algorithm for the coupling between three-dimensional and one-dimensional models. The coupling algorithm has been generalized in order to be applicable for junctions of m domains (e.g., one upstream domain, referred to in the following description by subscript index 1, and m−1 downstream domains). It is to be understood that that the models of these domains may be of any geometrical scale (e.g., 3-D, 1-D, and/or 0-D).

For the upstream model, a pressure boundary condition is considered, whereas for the downstream models, a flow rate boundary condition is applied. In the description that follows, superscript n refers to the solution at time step $t^n$, and superscript n+1 refers to the solution at time step $t^{n+1}$. Index k refers to the iterations performed at each time step in order to match the quantities of the m vessels.

1. Initialization: k=0, $$q_{i,0}^{n+1}=q_i^n,\ p_{i,0}^{n+1}=p_i^n,\ A_{i,0}^{n+1}=A_i^n,\ i=1\ldots m.$$

2. Loop on k
2.1. Compute the total flow rate to be distributed between the downstream vessels:

$$q_{2\div m,m+1}^{n+1} = \cdot q_{1,k}^{n+1} + (1-\chi)\sum_{i=2}^{m} q_{i,k}^{n+1}, \qquad (19)$$

where $\chi$ is a relaxation parameter.
2.2. Solve the downstream models using the following set of conditions:

$$\sum_{i=2}^{m} q_{i,k+1}^{n+1} = q_{2\div m,k+1}^{n+1}, \qquad (20a)$$

$$p_{i,k+1}^{n+1} = p_{i+1,k+1}^{n+1},\ i=2\ldots m-1. \qquad (20b)$$

As a result, $p_{i,k+1}^{n+1}$ and $q_{i,k+1}^{n+1}$, for $i=2\ldots m$, are determined.
2.3. Solve the upstream model using the boundary condition $$p_{1,k+1}^{n+1} = p_{2,k+1}^{n+1} \to q_{1,k+1}^{n+1}.$$

2.4. Set k=k+1.
3. Test for convergence: if $$\left| q_{1,k+1}^{n+1} - \sum_{i=2}^{m} q_{i,k+1}^{n+1} \right| < \varepsilon,$$

the solution scheme advances to the next time step (step 1), otherwise the iterative coupling algorithm reiterates at step 2.

In the above equations, the flow rate of the upstream vessel is considered to be positive in the outflow direction, whereas the flow rate of the downstream vessels is considered to be positive in the inflow direction.

The description that follows describes an application of the algorithm for the coupling between one-dimensional domains. In step 2.3, in order to apply the pressure boundary condition, the cross-sectional area at the outlet point of the upstream vessel $A_{1,k+1}^{n+1}$ may be determined given a certain pressure value. Thus, the state equation in EQNS. (11) and (12) is inverted. However, since it is unfeasible to analytically determine the inverse of the equation, the discretized version may be used:

$$p_{1,k+1}^{n+1} = \frac{4}{3}\frac{Eh}{r_0}\left(1 - \sqrt{\frac{A_0}{A_{1,k+1}^{n+1}}}\right) + \gamma\frac{A_{1,k+1}^{n+1} - A_1^n}{\Delta t} + p_0, \qquad (21)$$

$$\gamma = \frac{\gamma_S}{A_0\sqrt{A_{1,k+1}^{n+1}}}\ \text{or}\ \gamma = \frac{\gamma_S}{A_{1,k+1}^{n+1}\sqrt{A_{1,k+1}^{n+1}}}.$$

In order to solve this non-linear equation, the Newton-method is applied, and the unknown $A_{1,k+1}^{n+1}$ is initialized with the value at the previous iteration $A_{1,k}^{n+1}$.

If the algorithm is used to couple two vessels, or to couple a vessel and a Windkessel element (e.g., a lumped model in general)—in other words, m=2—step 2.2 may be simplified since there is only one downstream vessel. As a result EQN. (20b) is no longer required, and EQN. (20a) may be used directly in order to determine the flow rate to be imposed for the downstream vessel.

If m>2, as described below, a system of m−2 nonlinear equations is obtained, which may be solved using Newton's method. Using the negative characteristic, the following relationship may be written for each downstream vessel:

$$q_{i,k+1}^{n+1} = c_{i1}\cdot A_{i,k+1}^{n+1} - c_{i2},\ i=2\ldots m. \qquad (22)$$

wherein $c_{i1}$ and $c_{i2}$ are two constants obtained when rewriting the equation of the upstream characteristic into the form of EQN. (22). Next, by introducing EQN. (22) into EQN. (20b):

$$q_{2\div m,k+1}^{n+1} = \sum_{i=2}^{m}(c_{i1}\cdot A_{i,k+1}^{n+1} - c_{i2}) \to A_{m,k+1}^{n+1} = \qquad (23)$$

$$\frac{1}{c_{m1}}\left(q_{2\div m,k+1}^{n+1} - \sum_{i=2}^{m-1}(c_{i1}\cdot A_{i,k+1}^{n+1} - c_{i2}) - c_{m2}\right)$$

Thus, the system of EQN. (20b) may be written in extended form as:

$$\frac{4}{3}\left(\frac{Eh}{r_0}\right)_i\left(1 - \sqrt{\frac{(A_0)_i}{A_{i,k+1}^{n+1}}}\right) + (\gamma)_i\frac{A_{i,k+1}^{n+1} - A_i^n}{\Delta t} = \qquad (24a)$$

$$\frac{4}{3}\left(\frac{Eh}{r_0}\right)_{i+1}\left(1 - \sqrt{\frac{(A_0)_{i+1}}{A_{i+1,k+1}^{n+1}}}\right) + (\gamma)_{i+1}\frac{A_{i+1,k+1}^{n+1} - A_i^n}{\Delta t},\ i=2\ldots m-2$$

-continued $$\frac{4}{3}\left(\frac{Eh}{r_0}\right)_{m-1}\left(1-\sqrt{\frac{(A_0)_{m-1}}{A_{m-1,k+1}^{n+1}}}\right)+(\gamma)_{m-1}\frac{A_{m-1,k+1}^{n+1}-A_{m-1}^n}{\Delta t}= \quad (24b)$$

$$\frac{4}{3}\left(\frac{Eh}{r_0}\right)_m\left(1-\sqrt{\frac{(A_0)_m}{\frac{1}{c_{m1}}\left(q_{2\div m,k+1}^{n+1}-\sum_{i=2}^{m-1}(c_{i1}\cdot A_{i,k+1}^{n+1}-c_{i2})-c_{m2}\right)}}\right)+$$

$$(\gamma)_m\frac{\frac{1}{c_{m1}}\left(q_{2\div m,k+1}^{n+1}-\sum_{i=2}^{m-1}(c_{i1}\cdot A_{i,k+1}^{n+1}-c_{i2})-c_{m2}\right)-A_m^n}{\Delta t}.$$

Afterwards, the inlet flow rate of each downstream vessel may be computed using EQN. (22).

In case of a bifurcation—for example, m=3 (a regular bifurcation)—a single nonlinear equation that may be solved through Newton's method, is obtained:

$$\frac{4}{3}\left(\frac{Eh}{r_0}\right)_2\left(1-\sqrt{\frac{(A_0)_2}{A_{2,k+1}^{n+1}}}\right)+(\gamma)_2\frac{A_{2,k+1}^{n+1}-A_m^n}{\Delta t}= \quad (25)$$

$$\frac{4}{3}\left(\frac{Eh}{r_0}\right)_3\left(1-\sqrt{\frac{(A_0)_3}{\frac{1}{c_{31}}(q_{2\div 3,k+1}^{n+1}-(c_{21}\cdot A_{2,k+1}^{n+1}-c_{22})-c_{32})}}\right)+$$

-continued $$(\gamma)_{m-1}\frac{\frac{1}{c_{31}}(q_{2\div 3,k+1}^{n+1}-(c_{21}\cdot A_{2,k+1}^{n+1}-c_{22})-c_{32})-A_{m-1}^n}{\Delta t}.$$

Although the coupling algorithm refers to one upstream vessel and m−1 downstream vessels, there is no restriction regarding the direction of the flow in any of the junction vessels. The algorithm may be used for converging junctions as well as for diverging junctions.

The following examples and representative procedures illustrate features in accordance with the present teachings, and are provided solely by way of illustration. They are not intended to limit the scope of the appended claims or their equivalents.

In the examples described below, the following different constitutive wall models and implementation approaches are compared: elastic, viscoelastic V1 [EQN. (9)] applied at all grid points, viscoelastic V2 [EQN. (10)] applied at all grid points, viscoelastic V1 [EQN. (9)] applied only at interior points and elastic model at boundary points, and viscoelastic V2 [EQN. (10)] applied only at interior points and elastic model at boundary points. The latter two approaches will be referred to hereafter as V1-int and V2-int, respectively.

The parameters of the viscoelastic coefficient $\gamma_S$ have been set as follows: $T_S$=0.24s, $\Phi_S$=10°, σ=0.5 (corresponding to an incompressible material).

All junction and outflow points have been solved using a coupling algorithm in accordance with the present teachings as described above. The relaxation parameter χ was set to 0.5, and the tolerance threshold used for both the coupling algorithm and for the Newton iterations was set to 1e-8.

Figure 8:
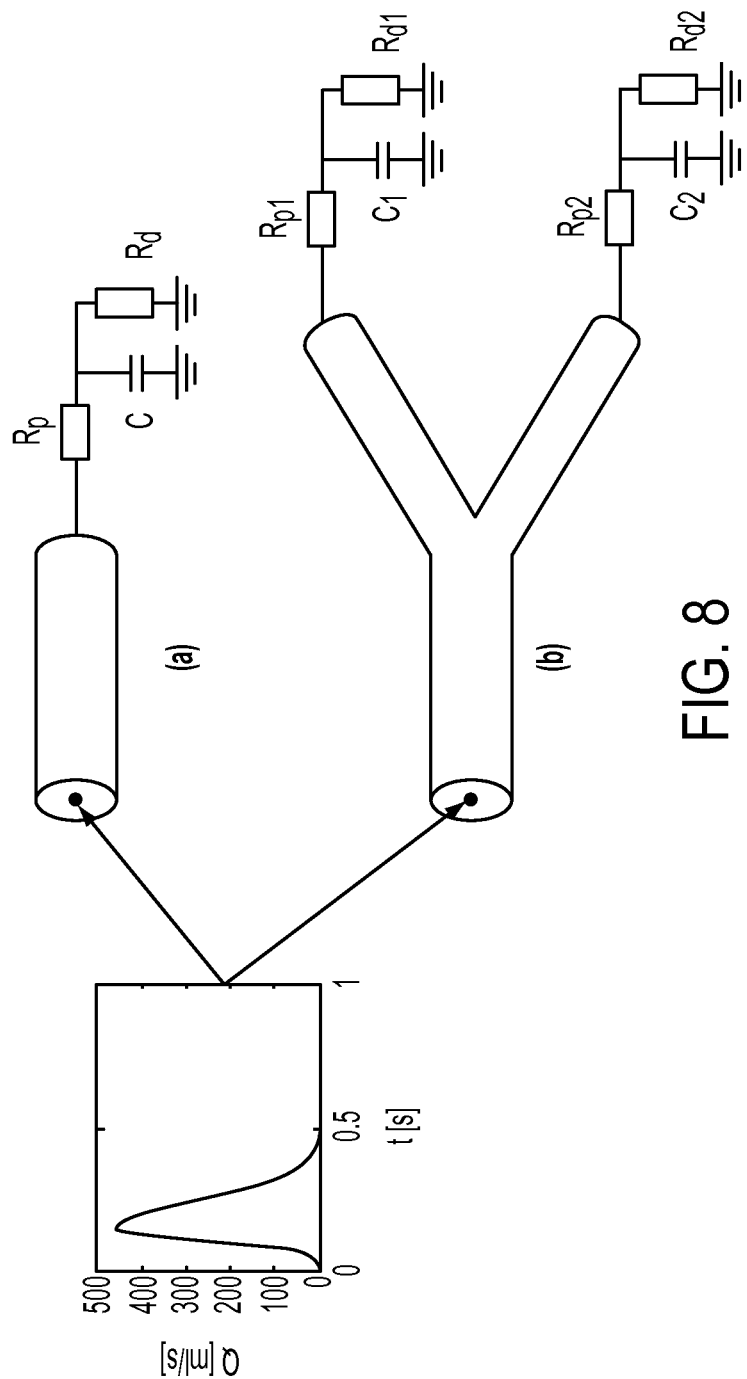
FIG. 8 shows a schematic illustration of (a) a single artery test case and (b) a bifurcation test case with a corresponding inlet flow rate profile and outflow boundary conditions.

Blood was modeled as an incompressible Newtonian fluid with a density of 1.055 g/cm$^3$ and a dynamic viscosity of 0.045 dyn-s/cm$^2$ for all of the computations. Two different test configurations were examined: (i) a single artery with an analytical time-varying inlet flow rate profile and Windkessel outflow boundary condition; and (ii) a bifurcation with an analytical time-varying inlet flow rate profile and Windkessel outflow boundary condition. The configurations and parameters of the two test cases are summarized in FIG. 8 and Table 1. The analytical time-varying inlet flow rate profile is given by an asymmetric Gaussian function with an average value of 80 ml/s. The sizes of these vessels resemble the proximal aortic segments. The grid space was set to 0.1 cm and the time step was set to 5e-5s in order to satisfy the CFL-condition for all three test cases. The initial pressure, $p_0$, was set to 60 mmHg, whereas the flow rate was initialized with zero at all grid points. The simulations were run for 15 cycles in order to obtain convergence.

TABLE 1

Single artery and Bifurcation test case simulation parameters.

| Test Case | | Length [cm] | Radius [cm] | $R_p$ [dynes · s/cm$^5$] | $R_p$ [dynes · s/cm$^5$] | C [10$^{-3}$ cm$^5$/ dynes] |
|---|---|---|---|---|---|---|
| Single Artery | | 3.0 | 1.25 | 100 | 1500 | 1.3 |
| Bifurcation | Daughter 1 | 3.0 | 1.05 | 150 | 2700 | 0.7 |
| | Daughter 1 | 3.0 | 0.95 | 180 | 3300 | 0.7 |

Figure 9A:
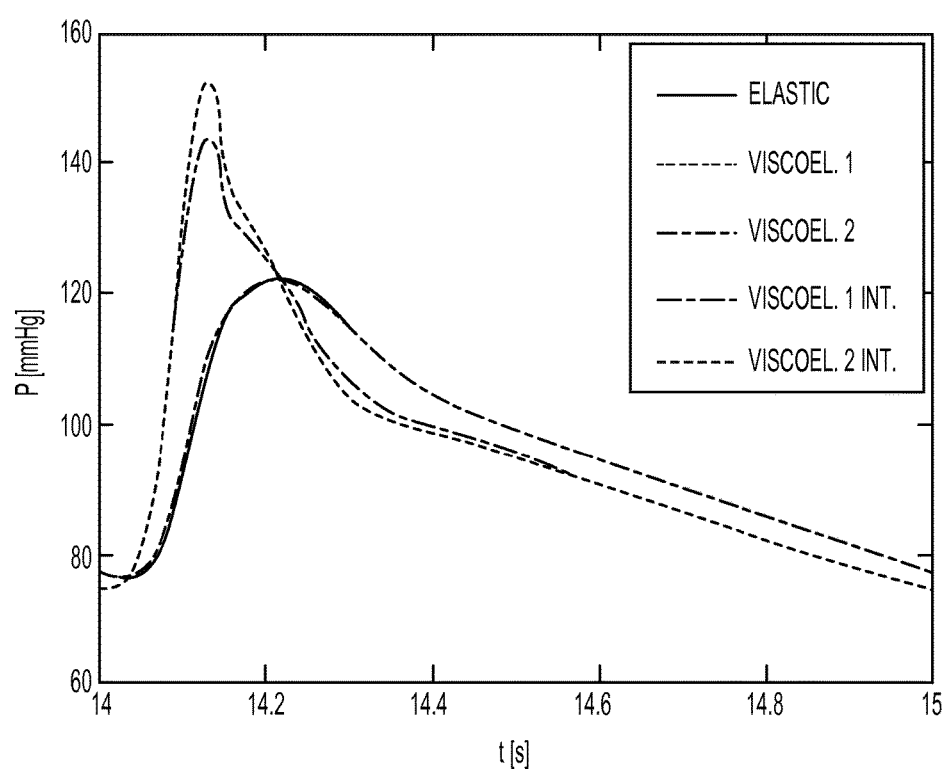
FIG. 9 shows plots of time-varying pressure, time-varying flow rate, and time-varying cross-sectional area comparing a single artery test case obtained with an elastic model to the models V1, V2, V1-int, and V2-int.
Figure 9B:
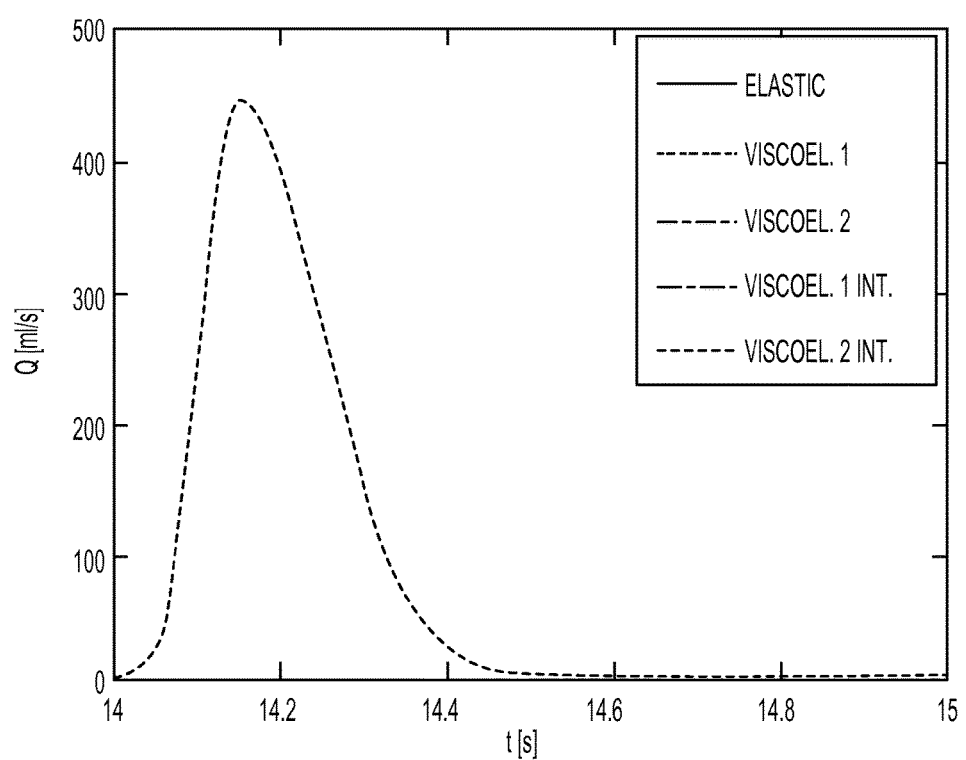
Figure 9C:
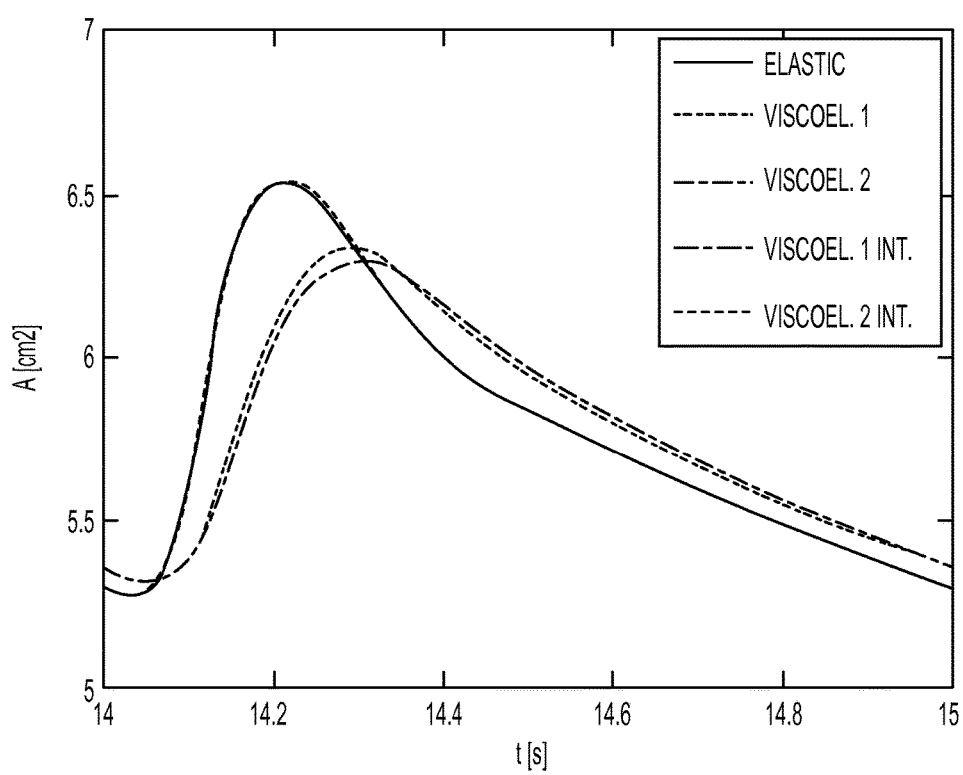
Figures 1, 10A:
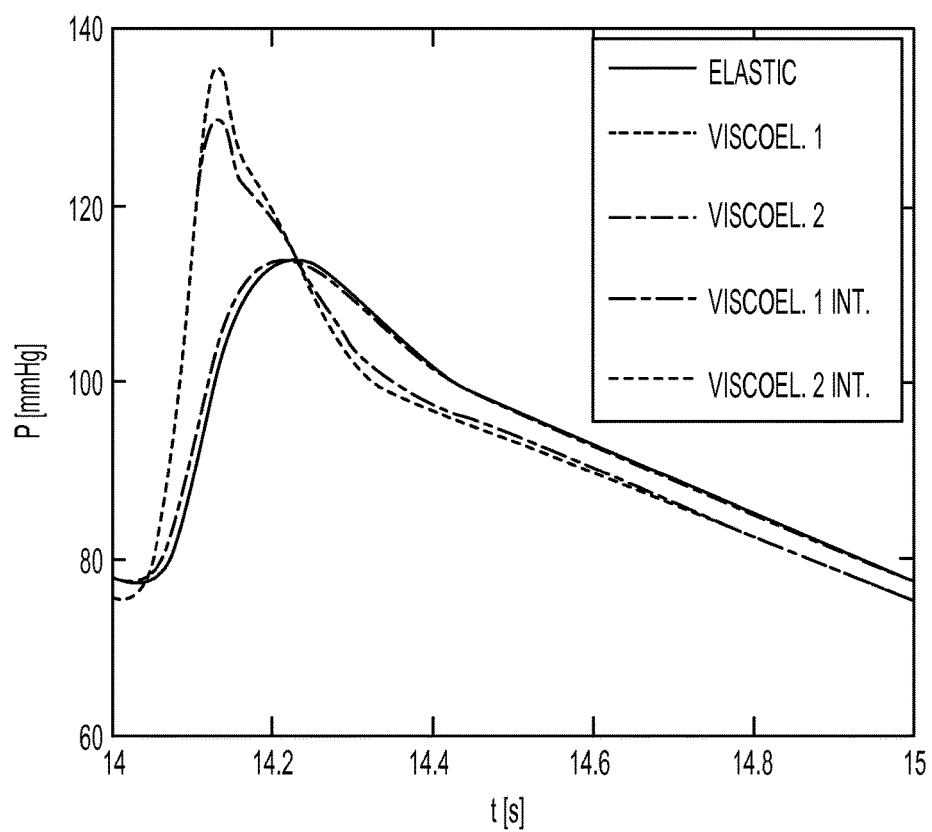
Figures 2, 10A:
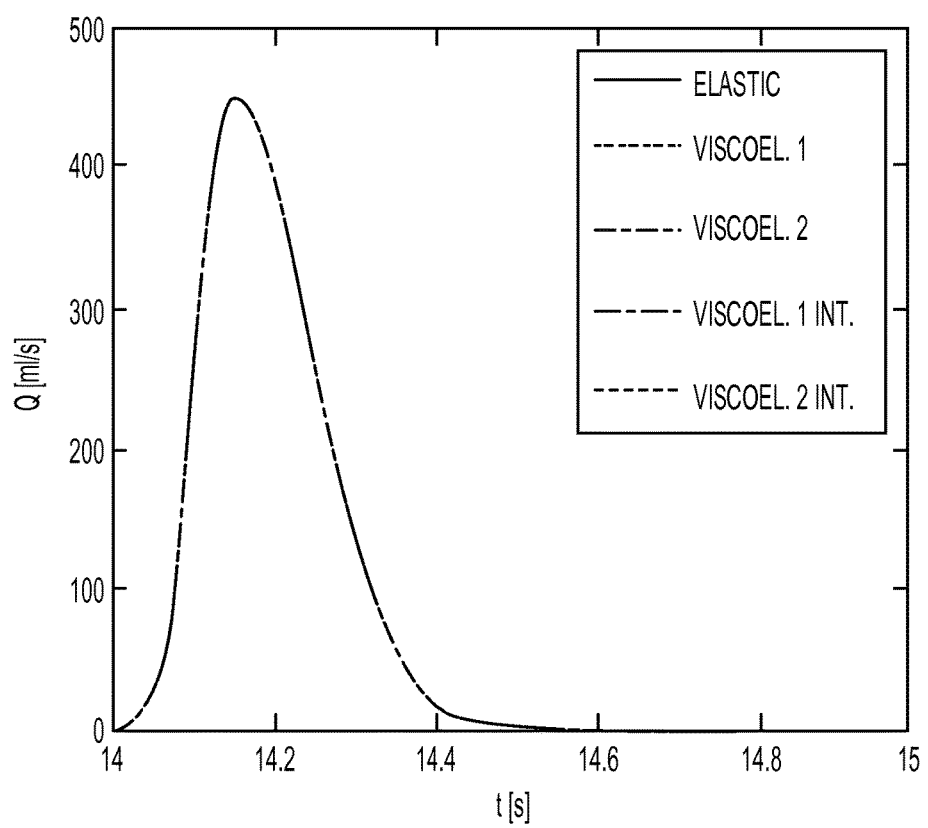
Figures 3, 10A:
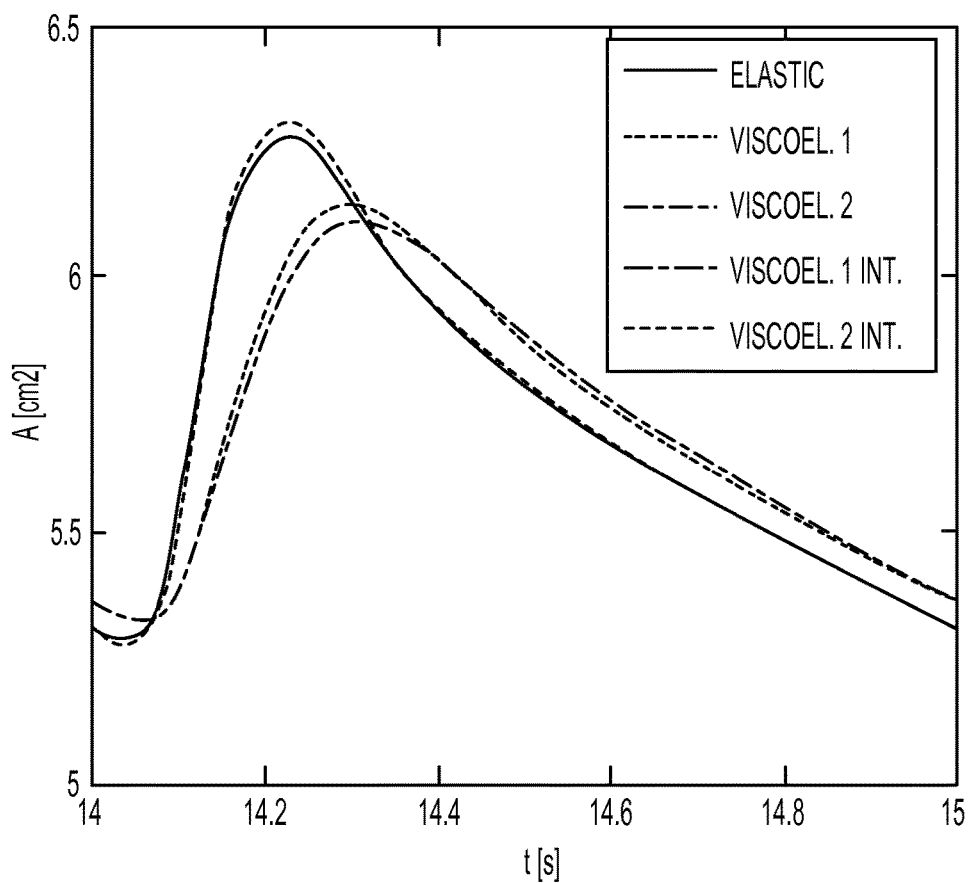
Figures 1, 10B:
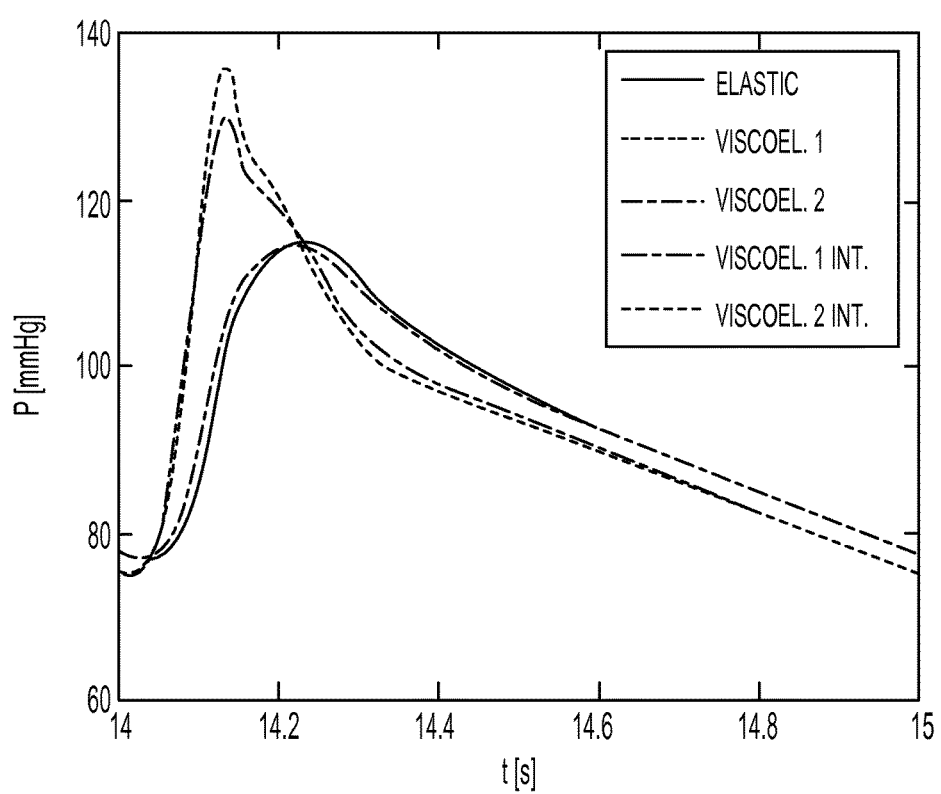
Figures 2, 10B:
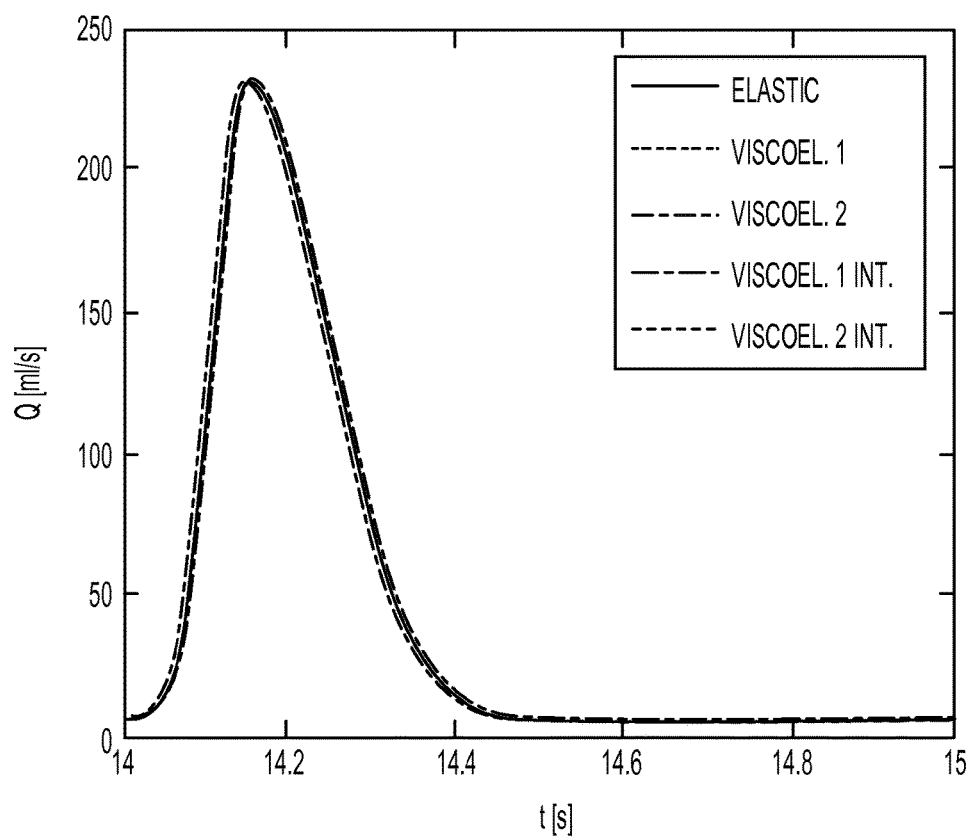
Figures 3, 10B:
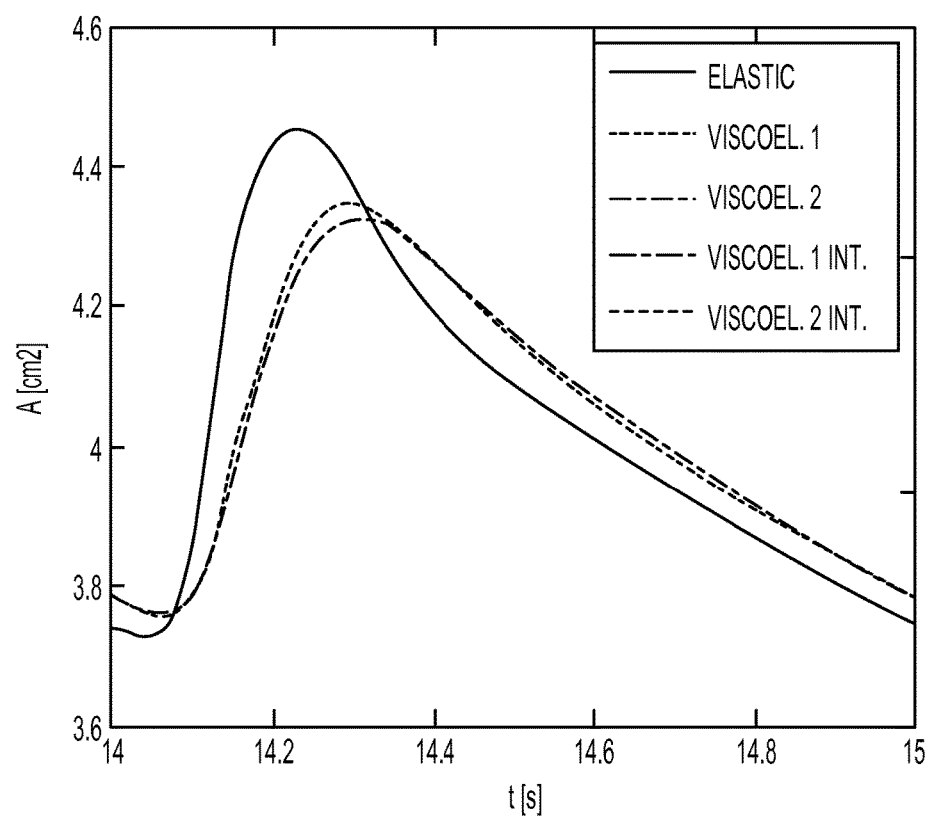
Figures 1, 10C:
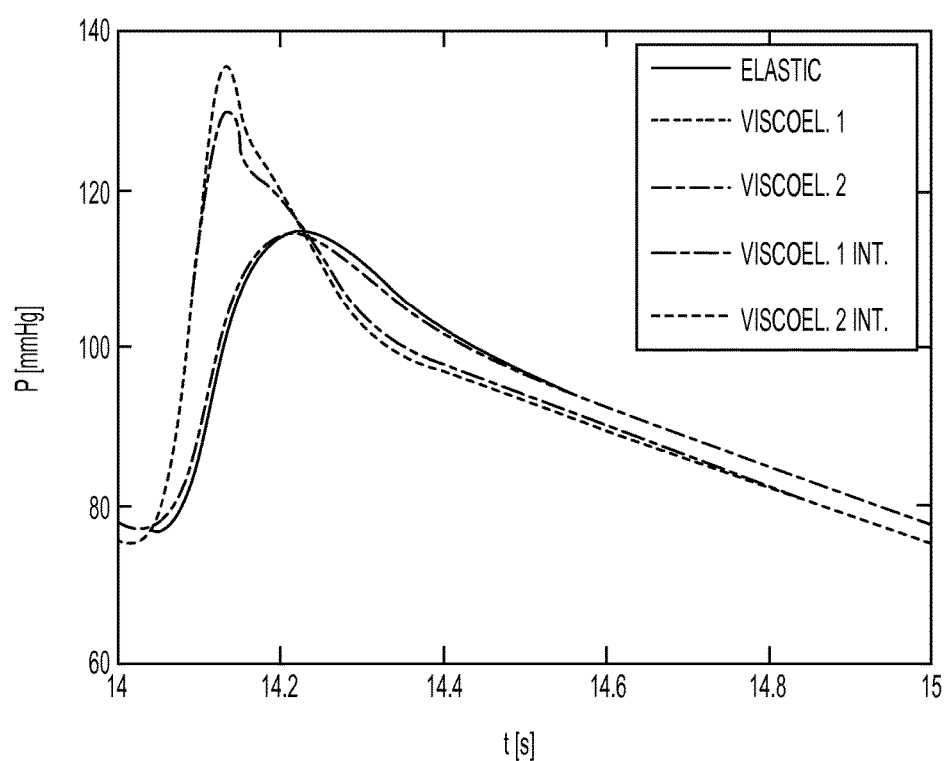
Figures 2, 10C:
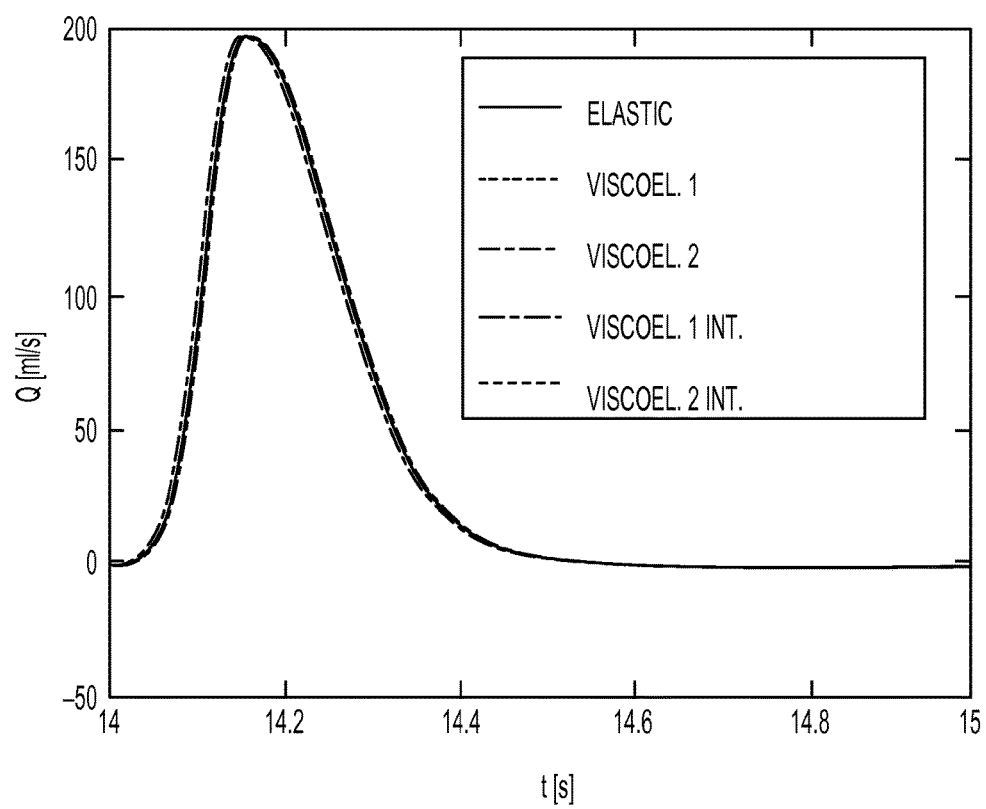
Figures 3, 10C:
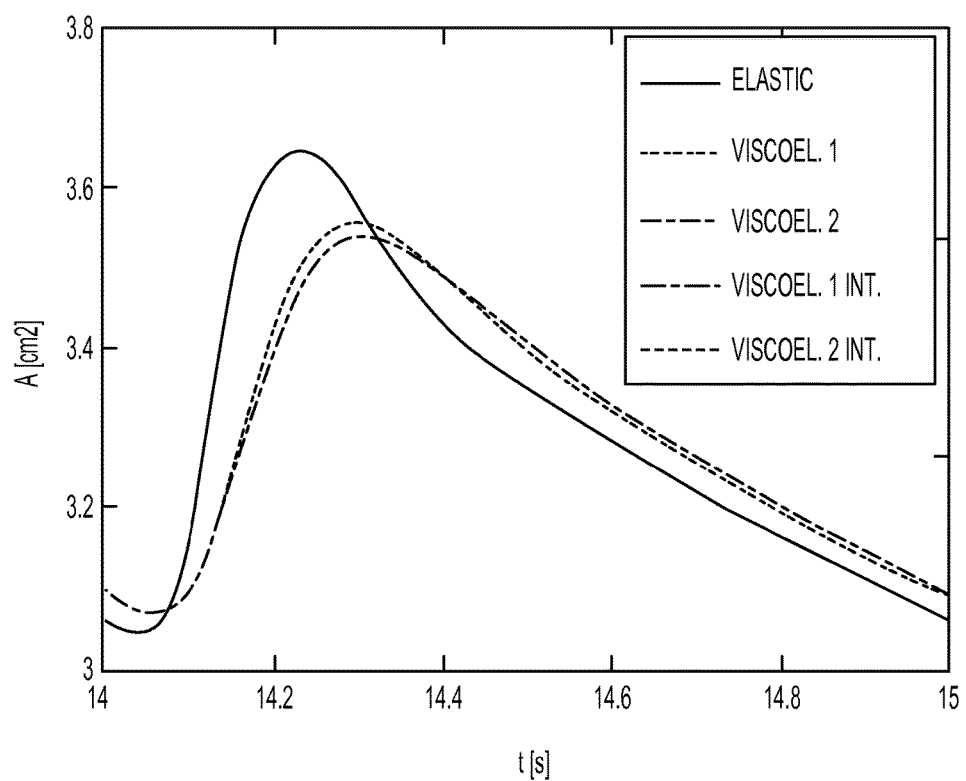

The results for the single artery test case are shown in FIG. 9 for the mid-vessel cross-section (at 1.5 cm). With respect to pressure, the results for the elastic model and for models V1 and V2 are similar. For models V1-int and V2-int, the pressure pulse is considerably higher (and higher for V2-int than for V1-int). Time-varying flow rate is identical for all five models. For the cross-sectional area, results are similar for the elastic model, and for models V1-int and V2-int. However, lower time-dependent variations are obtained when models V1 and V2 are used (with lower variations for V2 than for V1). Table 2 summarizes the differences between minimum and maximum pressure and cross-sectional area for the five different approaches.

TABLE 2

Difference between minimum and maximum pressures and cross-sectional areas using the single artery test case, obtained when applying the elastic model, and models V1, V2, V1-int, and V2-int.

| Measurement | Elastic | Viscoel. V1 | Viscoel. V2 | Viscoel. V1-interior points | Viscoel. V2-interior points |
|---|---|---|---|---|---|
| $P_{max}-P_{min}$ | 45.9 | 45.4 | 45.5 | 69.12 | 77.91 |
| $A_{max}-A_{min}$ | 1.28 | 1.03 | 0.98 | 1.28 | 1.28 |

The results for the bifurcation test case are shown in FIG. 10 for the mid-vessel cross-section (at 1.5 cm) of each vessel. The influence of the different constitutive wall models and different implementation types are similar to the single artery test case. Table 3 summarizes the differences between minimum and maximum pressure and cross-sectional area for the five different approaches. As before, the pressure pulse is much higher when models V1-int and V2-int are used, and the cross-sectional area variations are smaller for models V1 and V2.

TABLE 3

Difference between minimum and maximum pressures and cross-sectional areas using the bifurcation test case obtained when applying the elastic model, and models V1, V2, V1-int, and V2-int.

| Vessel | Measurement | Elastic | Viscoel. V1 | Viscoel. V2 | Viscoel. V1 - interior points | Viscoel. V2 - interior points |
|---|---|---|---|---|---|---|
| Parent | $P_{max}$-$P_{min}$ | 37.0 | 36.8 | 36.8 | 54.6 | 60.5 |
|  | $A_{max}$-$A_{min}$ | 0.99 | 0.83 | 0.79 | 1.03 | 1.02 |
| Daughter 1 | $P_{max}$-$P_{min}$ | 38.0 | 37.5 | 37.6 | 54.7 | 60.7 |
|  | $A_{max}$-$A_{min}$ | 0.72 | 0.59 | 0.57 | 0.73 | 0.73 |
| Daughter 2 | $P_{max}$-$P_{min}$ | 38.0 | 37.5 | 37.7 | 54.6 | 60.6 |
|  | $A_{max}$-$A_{min}$ | 0.59 | 0.49 | 0.47 | 0.59 | 0.59 |

Figure 11A:
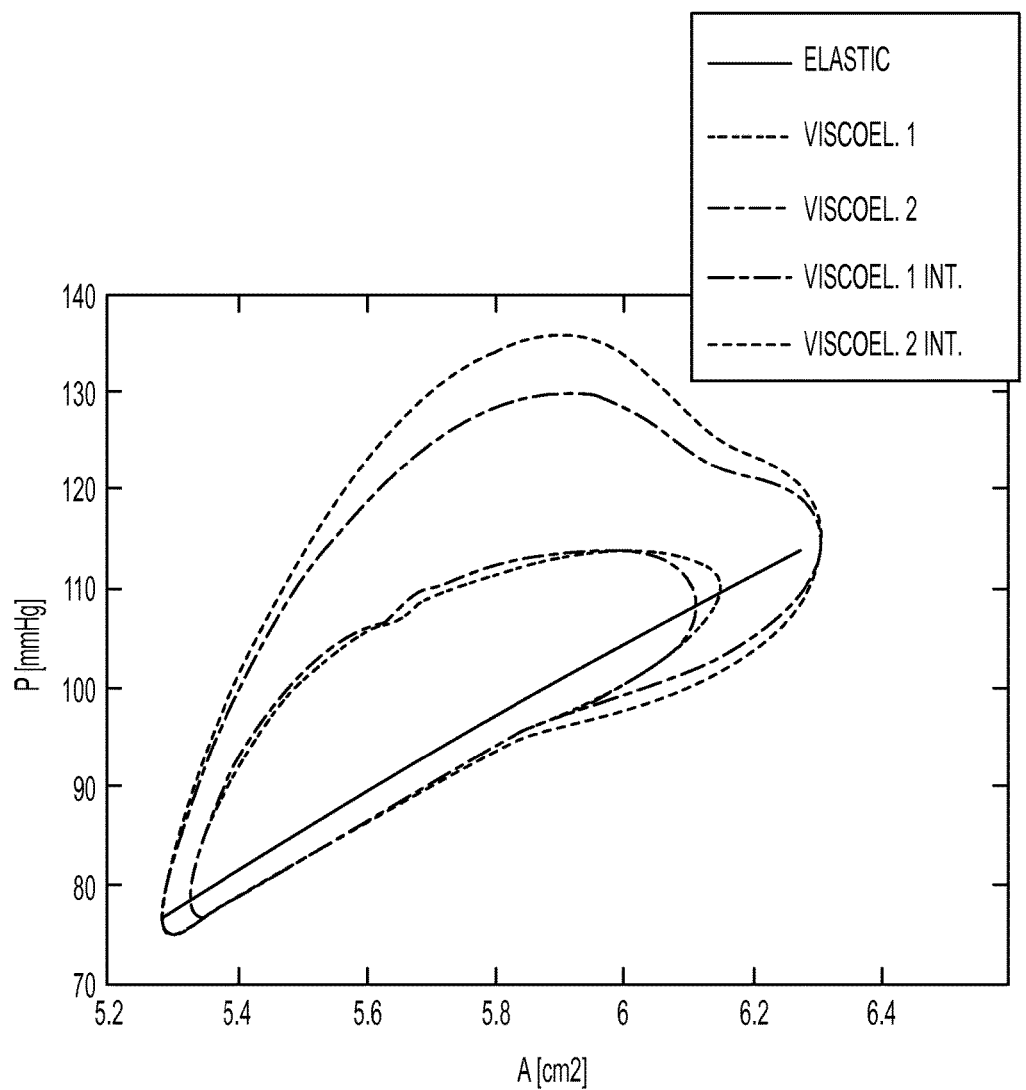
FIG. 11 shows plots of pressure vs. area relationships for the bifurcation test case. Data for the parent vessel are shown in (a), data for the daughter 1 vessel are shown in (b), and data for the daughter 2 vessel are shown in (c).
Figure 11B:
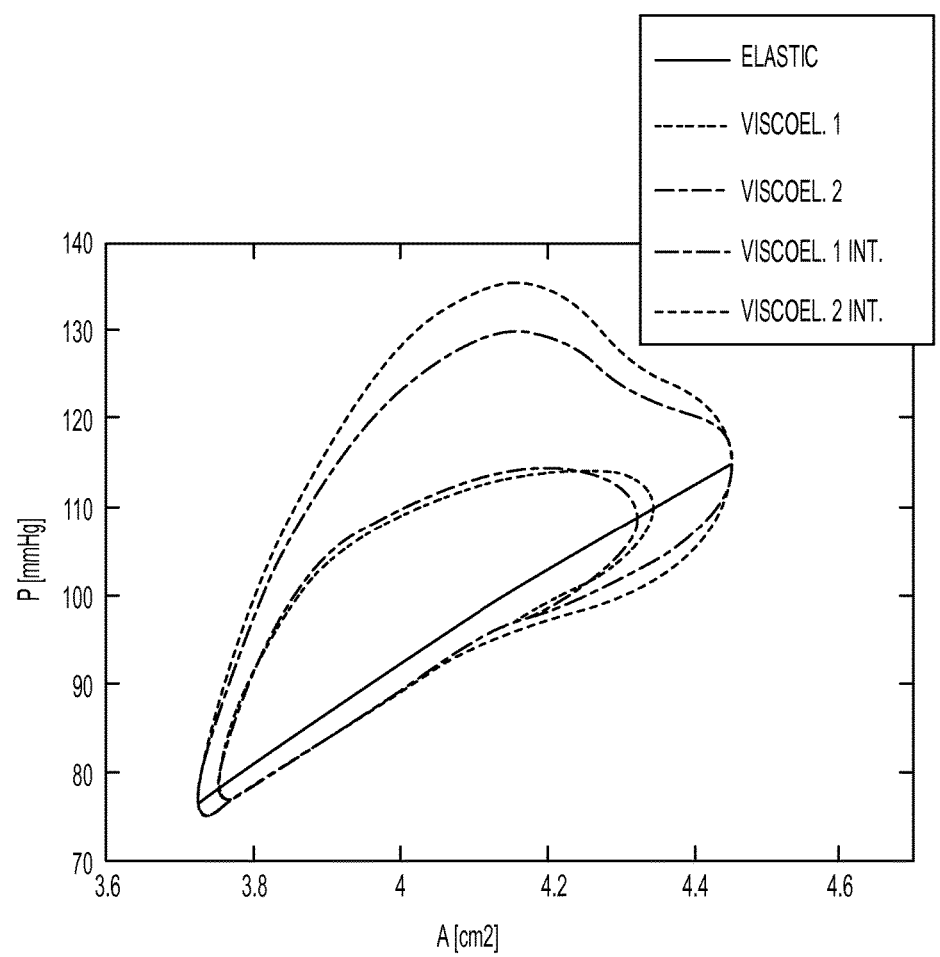
Figure 11C:
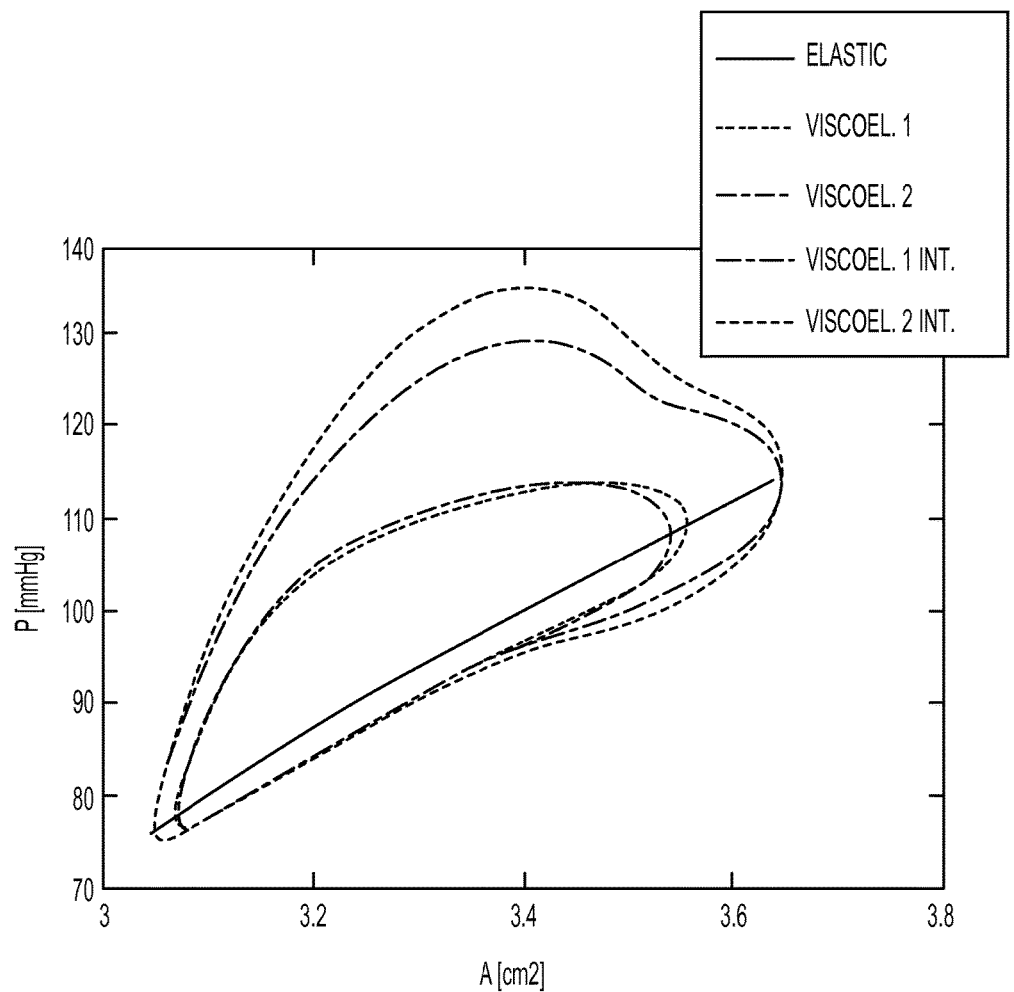

The pressure-area relationships for the three vessels of the bifurcation test case are shown in FIG. 11. As shown in FIG. 11, a hysteresis loop may be observed when viscoelastic wall models are used as opposed to the elastic wall model. The area of the hysteresis loop, which is proportional to the energy dissipation given by the viscoelastic properties of the wall, is much smaller for models V1 and V2 than for models V1-int and V2-int.

The above-described results obtained for the two test cases demonstrate the importance of considering the effect of viscoelasticity at the boundary points of a geometrical domain (e.g., inflow, branching, and outflow points). For simple geometries, consideration of the viscoelastic model at the boundary points may lead to lower variations in pressure and cross-sectional area. Moreover, pressure and flow rate are comparable to the results obtained with the elastic model. Only the cross-sectional area has a different time-dependent behavior.

A coupling algorithm in accordance with the present teachings may be used for the coupling of 3-D, 1-D, and/or 0-D domains, and for all manner of multi-scale coupling. As described above, while iteratively coupling the domains, a pressure boundary condition may be applied to the upstream domain and flow rate boundary conditions to the downstream domains. Since there is no restriction regarding the direction of the flow in any of the junction vessels, the type of boundary condition applied to the upstream and downstream vessels may be generally inverted. When applying the coupling algorithm for the coupling between a viscoelastic one-dimensional domain and a lumped model (e.g. Windkessel model), pressure is prescribed at the outflow of the 1D domain and flow rate at the inflow of the lumped domain. This stems from the fact that the main solution variables for the 1-D domain are the cross-sectional area and the flow rate. If the flow rate were imposed at the outlet, since an operator-splitting scheme with homogeneous Dirichlet boundary conditions for the viscous term of the flow rate is used, the algorithm would not converge. The pressure at the outlet of the 1-D domain is only computed using EQNS. (11) and (12) and is not part of the numerical scheme.

A recent study has compared two different viscoelastic models against an elastic model, for both a carotid artery and an abdominal aorta model. For these relatively simple geometries, conclusions similar to the present findings were drawn—namely, that time-varying pressure and flow rate are influenced less than the time-varying cross-sectional area when a viscoelastic model is employed as opposed to an elastic model. Moreover, the present studies have found that smaller variations in cross-sectional area are obtained when a viscoelastic model is used. Thus, the introduction of the viscoelastic term leads to not only smaller cross-sectional area variations but also to a phase shift between pressure and area, with the peak cross-sectional area being reached at a later moment inside the cardiac cycle.

In some embodiments, a method is provided for producing one-dimensional blood flow models with viscoelastic wall models. A coupling algorithm in accordance with the present teachings considers the effect of viscoelasticity at the inlet points, outlet points, and junction points of individual blood vessel segments. The coupling algorithm may be used together with an operator-splitting scheme for the solution of the one-dimensional blood flow model, thereby providing a fast computational approach. In some embodiments, the effect of viscoelasticity should not be neglected at bifurcation and outlet points, as demonstrated by results described herein. In some embodiments, a generalized form of the coupling algorithm may be likewise used for the coupling of 3-D/1-D/0-D domains.

One or more modules or logic described herein may be implemented using, among other things, a tangible computer-readable medium comprising computer-executable instructions (e.g., executable software code). Alternatively, modules may be implemented as software code, firmware code, hardware, and/or a combination of the aforementioned. For example the modules may be embodied as part of medical imaging system.

Figure 12:
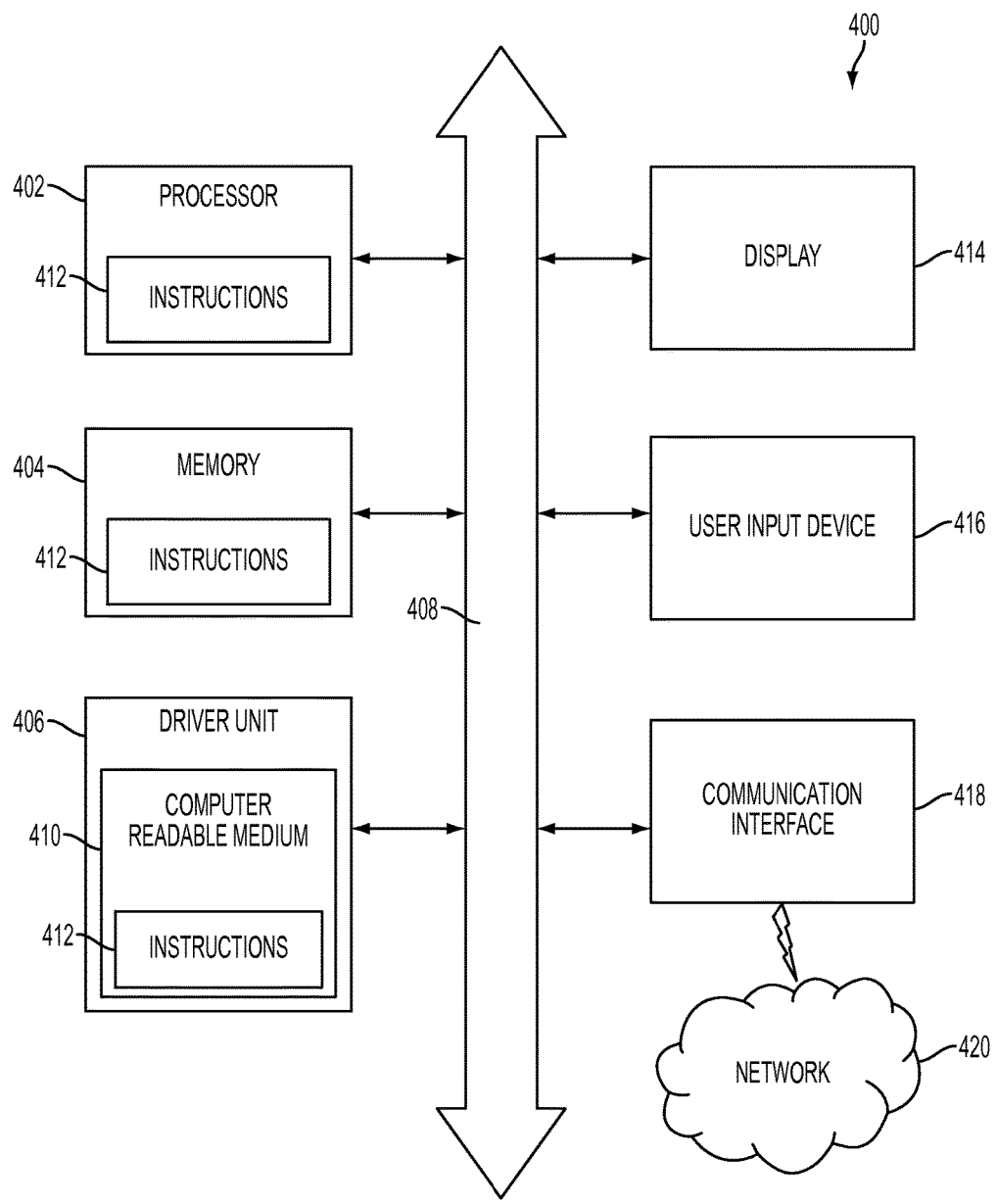
FIG. 12 shows a representative general computer system 400 for use with a system in accordance with the present teachings.

FIG. 12 depicts an illustrative embodiment of a general computer system 400. The computer system 400 may include a set of instructions that may be executed to cause the computer system 400 to perform any one or more of the methods or computer based functions disclosed herein. The computer system 400 may operate as a standalone device or may be connected (e.g., using a network) to other computer systems or peripheral devices. Any of the components discussed above, such as the processor, may be a computer system 400 or a component in the computer system 400. The computer system 400 may implement a modeling engine on behalf of a health care facility, of which the disclosed embodiments are a component thereof.

In a networked deployment, the computer system 400 may operate in the capacity of a server or as a client user computer in a client-server user network environment, or as a peer computer system in a peer-to-peer (or distributed)

network environment. The computer system 400 may also be implemented as or incorporated into various devices, such as a personal computer (PC), a tablet PC, a set-top box (STB), a personal digital assistant (PDA), a mobile device, a palmtop computer, a laptop computer, a desktop computer, a communications device, a wireless telephone, a land-line telephone, a control system, a camera, a scanner, a facsimile machine, a printer, a pager, a personal trusted device, a web appliance, a network router, switch or bridge, or any other machine capable of executing a set of instructions (sequential or otherwise) that specify actions to be taken by that machine. In some embodiments, the computer system 400 may be implemented using electronic devices that provide voice, video or data communication. Further, while a single computer system 400 is illustrated, the term "system" shall also be taken to include any collection of systems or sub-systems that individually or jointly execute a set, or multiple sets, of instructions to perform one or more computer functions.

As shown in FIG. 12, the computer system 400 may include a processor 402, for example a central processing unit (CPU), a graphics-processing unit (GPU), or both. The processor 402 may be a component in a variety of systems. For example, the processor 402 may be part of a standard personal computer or a workstation. The processor 402 may be one or more general processors, digital signal processors, application specific integrated circuits, field programmable gate arrays, servers, networks, digital circuits, analog circuits, combinations thereof, or other now known or later developed devices for analyzing and processing data. The processor 402 may implement a software program, such as code generated manually (i.e., programmed).

The computer system 400 may include a memory 404 that may communicate via a bus 408. The memory 404 may be a main memory, a static memory, or a dynamic memory. The memory 404 may include, but is not limited to, computer-readable storage media such as various types of volatile and non-volatile storage media, including but not limited to random access memory, read-only memory, programmable read-only memory, electrically programmable read-only memory, electrically erasable read-only memory, flash memory, magnetic tape or disk, optical media and the like. In some embodiments, the memory 404 includes a cache or random access memory for the processor 402. In alternative embodiments, the memory 404 is separate from the processor 402, such as a cache memory of a processor, the system memory, or other memory. The memory 404 may be an external storage device or database for storing data. Examples include a hard drive, compact disc (CD), digital video disc (DVD), memory card, memory stick, floppy disc, universal serial bus (USB) memory device, or any other device operative to store data. The memory 404 is operable to store instructions executable by the processor 402. The functions, acts or tasks illustrated in the figures or described herein may be performed by the programmed processor 402 executing the instructions 412 stored in the memory 404. The functions, acts or tasks are independent of the particular type of instructions set, storage media, processor or processing strategy and may be performed by software, hardware, integrated circuits, firm-ware, micro-code and the like, operating alone or in combination. Likewise, processing strategies may include multiprocessing, multitasking, parallel processing and the like.

As shown in FIG. 12, the computer system 400 may further include a display unit 414, such as a liquid crystal display (LCD), an organic light emitting diode (OLED), a flat panel display, a solid state display, a cathode ray tube (CRT), a projector, a printer or other now known or later developed display device for outputting determined information. The display 414 may act as an interface for the user to see the functioning of the processor 402, or specifically as an interface with the software stored in the memory 404 or in the drive unit 406. A value or image based on the modeling may be output to the user on the display unit 414. For example, an image representing part of the patient with modulation or alphanumeric text representing a calculated value is indicated in the image.

Additionally, as shown in FIG. 12, the computer system 400 may include an input device 416 configured to allow a user to interact with any of the components of system 400. The input device 416 may be a number pad, a keyboard, or a cursor control device, such as a mouse, or a joystick, touch screen display, remote control or any other device operative to interact with the system 400.

In some embodiments, as shown in FIG. 12, the computer system 400 may also include a disk or optical drive unit 406. The disk drive unit 406 may include a computer-readable medium 410 in which one or more sets of instructions 412 (e.g., software) may be embedded. Further, the instructions 412 may embody one or more of the methods or logic as described herein. In some embodiments, the instructions 412 may reside completely, or at least partially, within the memory 404 and/or within the processor 402 during execution by the computer system 400. The memory 404 and the processor 402 also may include computer-readable media as described above.

The present teachings contemplate a computer-readable medium that includes instructions 412 or receives and executes instructions 412 responsive to a propagated signal, so that a device connected to a network 420 may communicate voice, video, audio, images or any other data over the network 420. Further, the instructions 412 may be transmitted or received over the network 420 via a communication interface 418. The communication interface 418 may be a part of the processor 402 or may be a separate component. The communication interface 418 may be created in software or may be a physical connection in hardware. The communication interface 418 is configured to connect with a network 420, external media, the display 414, or any other components in system 400, or combinations thereof. The connection with the network 420 may be a physical connection, such as a wired Ethernet connection or may be established wirelessly as discussed below. Likewise, the additional connections with other components of the system 400 may be physical connections or may be established wirelessly.

The network 420 may include wired networks, wireless networks, or combinations thereof. The wireless network may be a cellular telephone network, an 802.11, 802.16, 802.20, or WiMax network. Further, the network 420 may be a public network, such as the Internet, a private network, such as an intranet, or combinations thereof, and may utilize a variety of networking protocols now available or later developed including, but not limited to TCP/IP based networking protocols.

Embodiments of the subject matter and the functional operations described in this specification may be implemented in digital electronic circuitry, or in computer software, firmware, or hardware, including the structures disclosed in this specification and their structural equivalents, or in combinations of one or more of them. Embodiments of subject matter described in this specification may be implemented as one or more computer program products, for example, one or more modules of computer program instructions encoded on a computer-readable medium for execution by, or to control the operation of, data processing apparatus. While the computer-readable medium is shown to be a single medium, the term "computer-readable medium" includes a single medium or multiple media, such as a centralized or distributed database, and/or associated caches and servers that store one or more sets of instructions. The term "computer-readable medium" shall also include any medium that is capable of storing, encoding or carrying a set of instructions for execution by a processor or that cause a computer system to perform any one or more of the methods or operations disclosed herein. The computer-readable medium may be a machine-readable storage device, a machine-readable storage substrate, a memory device, or a combination of one or more of them. The term "data processing apparatus" encompasses all apparatuses, devices, and machines for processing data, including but not limited to, by way of example, a programmable processor, a computer, or multiple processors or computers. The apparatus may include, in addition to hardware, code that creates an execution environment for the computer program in question (e.g., code that constitutes processor firmware, a protocol stack, a database management system, an operating system, or a combination thereof).

In some embodiments, the computer-readable medium may include a solid-state memory such as a memory card or other package that houses one or more non-volatile read-only memories. Further, the computer-readable medium may be a random access memory or other volatile re-writable memory. Additionally, the computer-readable medium may include a magneto-optical or optical medium, such as a disk or tapes or other storage device to capture carrier wave signals such as a signal communicated over a transmission medium. A digital file attachment to an e-mail or other self-contained information archive or set of archives may be considered a distribution medium that is a tangible storage medium. Accordingly, the present teachings are considered to include any one or more of a computer-readable medium or a distribution medium and other equivalents and successor media, in which data or instructions may be stored.

In some embodiments, dedicated hardware implementations, such as application specific integrated circuits, programmable logic arrays and other hardware devices, may be constructed to implement one or more of the methods described herein. Applications that may include the apparatus and systems of various embodiments may broadly include a variety of electronic and computer systems. One or more embodiments described herein may implement functions using two or more specific interconnected hardware modules or devices with related control and data signals that may be communicated between and through the modules, or as portions of an application-specific integrated circuit. Accordingly, the present system encompasses software, firmware, and hardware implementations.

In some embodiments, the methods described herein may be implemented by software programs executable by a computer system. Further, in some embodiments, implementations may include distributed processing, component/object distributed processing, and parallel processing. Alternatively, virtual computer system processing may be constructed to implement one or more of the methods or functionality as described herein.

Although the present teachings describe components and functions that may be implemented in particular embodiments with reference to particular standards and protocols, the present invention is not limited to such standards and protocols. For example, standards for Internet and other packet switched network transmission (e.g., TCP/IP, UDP/IP, HTML, HTTP, HTTPS) represent examples of the state of the art. Such standards are periodically superseded by faster or more efficient equivalents having essentially the same functions. Accordingly, replacement standards and protocols having the same or similar functions as those disclosed herein are considered equivalents thereof.

A computer program (also known as a program, software, software application, script, or code) may be written in any form of programming language, including compiled or interpreted languages, and it may be deployed in any form, including as a standalone program or as a module, component, subroutine, or other unit suitable for use in a computing environment. A computer program does not necessarily correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one computer or on multiple computers that are located at one site or distributed across multiple sites and interconnected by a communication network.

The processes and logic flows described herein may be performed by one or more programmable processors executing one or more computer programs to perform functions by operating on input data and generating output. The processes and logic flows may also be performed by, and apparatus may also be implemented as, special purpose logic circuitry, for example, an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The main elements of a computer are a processor for performing instructions and one or more memory devices for storing instructions and data. Generally, a computer will also include, or be operatively coupled to receive data from or transfer data to, or both, one or more mass storage devices for storing data, for example, magnetic, magneto optical disks, or optical disks. However, a computer need not have such devices. Moreover, a computer may be embedded in another device, for example, a mobile telephone, a personal digital assistant (PDA), a mobile audio player, a Global Positioning System (GPS) receiver, to name just a few. Computer-readable media suitable for storing computer program instructions and data include all forms of non volatile memory, media and memory devices, including but not limited to, by way of example, semiconductor memory devices (e.g., EPROM, EEPROM, and flash memory devices); magnetic disks (e.g., internal hard disks or removable disks); magneto optical disks; and CD ROM and DVD-ROM disks. The processor and the memory may be supplemented by, or incorporated in, special purpose logic circuitry.

To provide for interaction with a user, some embodiments of subject matter described herein may be implemented on a device having a display, for example a CRT (cathode ray tube) or LCD (liquid crystal display) monitor, for displaying information to the user and a keyboard and a pointing device, for example a mouse or a trackball, by which the user may provide input to the computer. Other kinds of devices may be used to provide for interaction with a user as well. By way of example, feedback provided to the user may be any form of sensory feedback (e.g., visual feedback, auditory feedback, or tactile feedback); and input from the user may be received in any form, including but not limited to acoustic, speech, or tactile input.

Embodiments of subject matter described herein may be implemented in a computing system that includes a back-end component, for example, as a data server, or that includes a middleware component, for example, an application server, or that includes a front end component, for example, a client computer having a graphical user interface or a Web browser through which a user may interact with an implementation of the subject matter described in this specification, or any combination of one or more such back end, middleware, or front end components. The components of the system may be interconnected by any form or medium of digital data communication, for example, a communication network. Examples of communication networks include but are not limited to a local area network (LAN) and a wide area network (WAN), for example, the Internet.

The computing system may include clients and servers. A client and server are generally remote from each other and typically interact through a communication network. The relationship of client and server arises by virtue of computer programs running on the respective computers and having a client-server relationship to each other.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

While this specification contains many specifics, these should not be construed as limitations on the scope of the invention or of what may be claimed, but rather as descriptions of features specific to particular embodiments. Certain features that are described in this specification in the context of separate embodiments may also be implemented in combination in a single embodiment. Conversely, various features that are described in the context of a single embodiment may also be implemented in multiple embodiments separately or in any suitable sub-combination. Moreover, although features may be described above as acting in certain combinations and even initially claimed as such, one or more features from a claimed combination may in some cases be excised from the combination, and the claimed combination may be directed to a sub-combination or variation of a sub-combination.

Similarly, while operations are depicted in the drawings and described herein in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems may generally be integrated together in a single software product or packaged into multiple software products.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is provided to comply with 37 CFR § 1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding claim—whether independent or dependent—and that such new combinations are to be understood as forming a part of the present specification.

The foregoing detailed description and the accompanying drawings have been provided by way of explanation and illustration, and are not intended to limit the scope of the appended claims. Many variations in the presently preferred embodiments illustrated herein will be apparent to one of ordinary skill in the art, and remain within the scope of the appended claims and their equivalents.

The invention claimed is:

1. A computer-implemented method for modeling a blood vessel, the method comprising:
    modeling, by a processor, a first segment and a second segment of the blood vessel based on medical imaging data acquired from a patient;
    computing, by the processor, a first modeling parameter at an interior point of the first segment;
    computing, by the processor iteratively with the computing of the first modeling parameters at the interior point, a second modeling parameter at a boundary point of the first segment, the second modeling parameter being a function of a viscoelastic wall model defined by a value for a viscoelastic term modeling viscoelastic behavior of a wall of the blood vessel and a value for an elastic term modeling elastic behavior of the wall of the blood vessel, the computing of the second modeling parameter comprising sequentially solving for the viscoelastic term and elastic term in an operator-splitting scheme;

coupling, by the processor, a first domain of the first segment of the blood vessel to a second domain of the second segment of the blood vessel using the viscoelastic wall model at the first domain and at the second domain, wherein the first domain comprises the boundary point and the second domain comprises a second boundary point of the second segment; and generating an image representing the patient, a value of the first modeling parameter, and a value of the second modeling parameter, the image having modulation or alphanumeric text of the values of the first and second modeling parameters, the values of the first and second modeling parameters responsive to the coupling, wherein the first modeling parameter comprises a patient-specific parameter indicative of the patient's anatomy, physiology, or hemodynamics of the first segment.

2. The computer-implemented method of claim 1 wherein a model obtained by the modeling of the first segment comprises a zero-dimensional model, a one-dimensional model, a three-dimensional model, or a combination thereof.

3. The computer-implemented method of claim 1 wherein a model obtained by the modeling of the first segment comprises a one-dimensional model.

4. The computer-implemented method of claim 1 wherein the medical imaging data is selected from the group consisting of magnetic resonance data, computed tomography data, positron emission tomography data, single photon emission tomography data, ultrasound data, angiographic data, x-ray data, and combinations thereof.

5. The computer-implemented method of claim 1 wherein the computing, by the processor, of the first modeling parameter at the interior point of the first segment uses the viscoelastic wall model.

6. The computer-implemented method of claim 5 further comprising implementing, by the processor, the operator-splitting scheme the elastic term is solved sequentially prior to the viscoelastic term.

7. The computer-implemented method of claim 6 wherein the first modeling parameter is selected from the group consisting of a cross-sectional area, an elastic component of a flow rate, a viscoelastic component of the flow rate, a total flow rate, and combinations thereof.

8. The computer-implemented method of claim 1 wherein the boundary point is selected from the group consisting of an inflow point, a junction point, an outflow point, and combinations thereof.

9. The computer-implemented method of claim 8 wherein the junction point is selected from the group consisting of a bifurcation, a trifurcation, a quadfurcation, a pentafurcation, a hexafurcation, and combinations thereof.

10. The computer-implemented method of claim 1 wherein the second modeling parameter is selected from the group consisting of a cross-sectional area, a flow rate, and a combination thereof.

11. The computer-implemented method of claim 1 wherein a geometrical scale of the first domain is different than a geometrical scale of the second domain.

12. The computer-implemented method of claim 1 wherein the computing, by the processor, of the first modeling parameter comprises:

computing, by the processor, a cross-sectional area at the interior point;

computing, by the processor, an elastic component of a flow rate at the interior point;

computing, by the processor, a viscoelastic component of the flow rate at the interior point; and computing, by the processor, a total flow rate at the interior point.

13. The computer-implemented method of claim 1 wherein the computing, by the processor, of the second modeling parameter comprises:

computing, by the processor, a cross-sectional area at the boundary point.

14. The computer-implemented method of claim 13 wherein the computing, by the processor, of the second modeling parameter further comprises:

computing, by the processor, a flow rate at the boundary point.

15. The computer-implemented method of claim 1 further comprising implementing, by the processor, the operator-splitting scheme with conservation of mass and conservation of momentum in the first segment of the blood vessel.

16. A system for modeling a blood vessel, the system comprising:

a processor;

a non-transitory memory coupled with the processor;

first logic stored in the non-transitory memory and executable by the processor to cause the processor to model a first segment and a second segment of the blood vessel based on medical imaging data acquired from a subject;

second logic stored in the non-transitory memory and executable by the processor to cause the processor to compute a first modeling parameter at an interior point of the first segment;

third logic stored in the non-transitory memory and executable by the processor to cause the processor to compute a second modeling parameter at a boundary point of the first segment using a viscoelastic wall model defined by a value for a viscoelastic term modeling viscoelastic behavior of a wall of the blood vessel and a value for an elastic term modeling elastic behavior of the wall of the blood vessel, the computation of the second modeling parameter comprising sequential solution for the viscoelastic term and elastic term in an operator-splitting scheme;

fourth logic stored in the non-transitory memory and executable by the processor to cause the processor to couple a first domain of the first segment of the blood vessel to a second domain of the second segment of the blood vessel using the viscoelastic wall model at the first domain and at the second domain, wherein the first domain comprises the boundary point and the second domain comprises a second boundary point of the second segment; and a display configured to display an image representing the subject, a value of the first modeling parameter, and a value of the second operating parameter, the image being based on the coupling, and the first modeling parameter comprising a patient-specific parameter indicative of the patient's anatomy, physiology, or hemodynamics of the first segment.

17. The system of claim 16 wherein computation of the first modeling parameter by execution of the second logic uses the viscoelastic wall model.

18. The system of claim 16 wherein the boundary point is selected from the group consisting of an inflow point, a junction point, an outflow point, and combinations thereof.

19. The system of claim 16 wherein the third logic further comprises implementing the operator-splitting scheme with conservation of mass and conservation of momentum in the first segment of the blood vessel.

20. A non-transitory computer-readable storage medium having stored therein data representing instructions executable by a programmed processor for modeling a blood vessel, the storage medium comprising instructions for:
- modeling a first segment and a second segment of the blood vessel based on medical imaging data acquired from a subject;
- computing a first modeling parameter at an interior point of the first segment;
- computing a second modeling parameter at a boundary point of the first segment with a viscoelastic wall model defined by a value for a viscoelastic term modeling viscoelastic behavior of a wall of the blood vessel and a value for an elastic term modeling elastic behavior of the wall of the blood vessel, the computing of the second modeling parameter comprising sequentially solving for the viscoelastic term and elastic term in an operator-splitting scheme;
- coupling a first domain of the first segment of the blood vessel to a second domain of the second segment of the blood vessel using the viscoelastic wall model at the first domain and at the second domain, wherein the first domain comprises the boundary point and the second domain comprises a second boundary point of the second segment; and
- generating an image representing the subject, a value of the first modeling parameter, and a value of the second modeling parameter, the image being based on the coupling.

21. The non-transitory computer-readable storage medium of claim 20 further comprising instructions for implementing the operator-splitting scheme with conservation of mass and conservation of momentum in the first segment of the blood vessel.

* * * * *